United States Patent [19]
Ratner et al.

[11] Patent Number: 5,171,267
[45] Date of Patent: Dec. 15, 1992

[54] SURFACE-MODIFIED SELF-PASSIVATING INTRAOCULAR LENSES

[75] Inventors: Buddy D. Ratner, Seattle, Wash.; Caren L. Tidwell, J.C. Arnhem, Netherlands

[73] Assignee: The Board of Regents of the University of Washington, Seattle, Wash.

[21] Appl. No.: 675,600

[22] Filed: Mar. 25, 1991

Related U.S. Application Data

[63] Continuation-in-part of Ser. No. 402,181, Aug. 31, 1989, Pat. No. 5,002,794.

[51] Int. Cl.$^5$ .......................... A61F 2/16; A01N 1/02
[52] U.S. Cl. .......................................... 623/6; 427/2; 427/425; 427/491
[58] Field of Search ................. 623/6, 66, 901; 427/2, 427/38-41, 425

[56] References Cited

U.S. PATENT DOCUMENTS

| | | | |
|---|---|---|---|
| 3,475,307 | 10/1969 | Knox et al. | 117/93.1 |
| 4,132,829 | 1/1979 | Hudis | 428/411 |
| 4,212,719 | 7/1980 | Osada et al. | 204/165 |
| 4,419,382 | 12/1983 | Sliemers | 427/40 |
| 4,424,311 | 1/1984 | Nagaoka et al. | 259/4 |
| 4,530,974 | 7/1985 | Munro et al. | 525/329.4 |
| 4,569,858 | 2/1986 | Lim et al. | 427/164 |
| 4,655,770 | 4/1987 | Gupta et al. | 623/1 |
| 4,656,083 | 4/1987 | Hoffman et al. | 428/265 |
| 4,705,612 | 11/1987 | Shimomura et al. | 204/165 |
| 4,718,905 | 1/1988 | Freeman | 623/6 |
| 4,822,359 | 4/1989 | Tano et al. | 623/6 |
| 4,955,901 | 9/1990 | Nishiguchi et al. | 623/6 |
| 4,979,959 | 12/1990 | Guire | 623/66 |
| 5,002,794 | 3/1991 | Ratner et al. | 427/41 |
| 5,007,928 | 4/1991 | Okamura et al. | 623/6 |

FOREIGN PATENT DOCUMENTS

62250/86 3/1985 Australia .
57-164064 10/1982 Japan .

OTHER PUBLICATIONS

Yasuda et al., "Plasma Polymerization Investigated by the Substrate Temperature Dependence," *Journal of Polymer Science: Polymer Chemistry Edition,* 23:87-106 (1985).

Sherman, A., "Plasma-Assisted Chemical Vapor Deposition Processes and Their Semiconductor Applications," *Thin Solid Films,* 113:135-149 (1984).

Munro et al., "The Influence of Power and Substrate Temperature on Chemical Composition, Determined by ESCA, of the Inductively Coupled RF Plasma Polymerization of Acrylonitrile," *Journal of Polymer Science: Polymer Chemistry Edition,* vol. 23, 479-499 (1985).

Czornyi, G., "The Effect of Temperature on the Morphology of Plasma Polymerized Fluorocarbon Films," *ACS Org. Coatings Appl. Polym. Proc.,* 47:457-461 (1982).

Witt et al., "Convenient Direct Synthesis of $(SN)_x$ Films From $S_4N_4$ at Lower Temperatures", *American Chemical Society,* pp. 1668-1669 (1983).

Merrill et al., "Polyether Networks: Fibrinogen Adsorption and Platelet Retention," *The 11th Annual Meeting of the Society for Biomaterials,* 106 (1985).

Nagaoka et al., "Interaction Between Blood Components and Hydrogels With Poly(oxyethylene)Chains," *Polymers as Biomaterials,* 8352:361-375 (1984).

Merrill et al., "Polyethylene Oxide as a Biomaterial," *American Society for Artificial Internal Organs,* 2:60-64 (1983).

(List continued on next page.)

Primary Examiner—Ronald Frinks
Attorney, Agent, or Firm—Christensen, O'Connor, Johnson & Kindness

[57] ABSTRACT

The invention relates to intraocular lenses coated with $C_{12}-C_{36}$ alkyl groups that render the surface of the intraocular lens less prone to causing inflammation after implantation of the intraocular lens. The alkyl groups may be coated on the IOL by a centrifugal casting method, a solution deposition method (e.g., a covalent attachment method), or a plasma deposition method that minimizes fragmentation of the alkyl groups.

19 Claims, 6 Drawing Sheets

OTHER PUBLICATIONS

Ho Lee et al., "Protein-Resistant Surfaces Prepared by PEO-Containing Block Copolymer Surfactants," *Journal of Biomedical Materials Research*, 23:351–368 (1989).

Nojiri et al., "In Vivo Protein Adsorption Onto Polymers: A Transmission Electron Microscopic Study," *Trans Am. Soc. Artif. Intern. Organs*, XXV:357–361 (1989).

Maechling-Strasser et al. "Synthesis and Adsorption of a Poly(N-Acetylethyleneimine)-Polyethyleneoxide-Poly(N-Acetylethyleneimine) Triblock-Copolymer at a Silica/Solution Interface. Influence of Its Preadsorption on Platelet Adhesion and Fibrinogen Adsorption," *Journal of Biomedical Materials Research*, 23:1395–1410 (1989).

Andrade et al., "Surfaces and Blood Compatibility Current Hypotheses," *Trans. Am. Soc. Artif. Intern. Organs*, XXXIII:75–84 (1987).

Marmur et al., "Sedimentation and Adhesion of Blood Platelets Under a Centrifugel Force," *Journal of Colloid and Interface Science*, 104:390–397 (1985).

Nishimura et al., "Adhesion Behavior of Rat Lymphocytes on Poly(g-Benzyl L-Glutamate) Derivatives Having Hydroxyl Groups or Poly(Ethylene Glycol) Chains", *Makromol. Chem.*, 185:2109–2116 (1984).

Akizawa et al., "Efficiency and Biocompatibility of a Polyethlyene Glycol Grafted Cellulosic membrane During Hemodialysis," *Trans. Am. Soc. Artif. Intern. Organs*, XXXV:333–335 (1989).

Bots et al., "Small Diameter Blood Vessel Prostheses From Blends of Polyethylene Oxide and Polypropylene Oxide," *Biomaterials*, 7(5):393–399 (1986).

Ho Lee et al., "Surface Properties of Aqueous Peo-Containing Block Copolymer Surfactants: Protein-Resistant Surfaces," *ACS Polym. Mat. Sci. and Eng.*, 57:613–617 (1987).

Sun et al., "Non-Fouling Biomaterial Surfaces: II. Protein Adsorption on Radiation Grafted Polyethylene Glycol Methacrylate Copolymers," *ACS Polymer Reprints*, 23(1):292–294 (1987).

Courtney et al., "Measurement of Platelet Loss in the blood Compatibility Assessment of Biomaterials," *Biomaterials*, 8:231–232 (1987).

Tsai et al., "Enhanced Albumin Affinity of Silicone Rubber", *Trans. Am Soc. Intern. Organs*, XXXIV:559–563 (1988).

Eberhart et al., "Albumin Adsorption and Retention on $C_{18}$-Alkyl-Derivatized Polyurethane Vascular Grafts," *Artificial Organs*, 11(5):375–382 (1987).

Pitt et al., "Albumin Adsorption on Alkyl Chain Derivatized Polyurethanes: I. The Effect of C-18 Alkylation," *Journal of Biomedical Materials Research*, 22:359–382 (1988).

Pitt et al., "Albumin Adsorption on Alkyl Chain Derivatized Polyurethanes," *Journal of Biomedical Materials Research*, 9:36–346 (1988).

Munro et al., "Thromboresistant Alkyl Derivatized Polyurethanes," *American Society for Artificial Organs*, 6:65–75 (1983).

Yasuda, H., "Glow Discharge Polymerization," *Journal of Polymer Science:Macromolecular Reviews*, 16:199–293 (1981).

Lee, J. H. et al., "Surface Properties of Aqueous Peo-Containing Block Copolymer Surfactant: Protein Resistant Surfaces," *Department of Materials Science and Engineering*, University of Utah, USA (1987).

Sun, Y. et al., "Non-fouling Biomaterial Surfaces: II. Protein Adsorption on Radiation Grafted Polyethylene Glycol Methacrylate Copolymers," *ACS Polymer Reprints*, 28(1):292–294 (1987).

Gombotz, W. R. et al., "Immobilization of Poly(ethylene Oxide) on Poly(ethylene Terephthalate) Using a Plasma Polymerization Process," *Journal of Applied Polymer Science*, 37:91–107 (1989).

Yasuda, H. et al., "Plasma Polymerization of Some Organic Compounds and Properties of the Polymers," *Journal of Polymer Science: Polymer Chemistry Section*, 14:195–224 (1976).

Lopez, G. P. et al., "Effect of Reduced Substrate Temperature on Film Chemistry in Plasma Deposition of Organics," Abstract Submission Form for ISPC-9 Italy (Pugnochiuso) 1989.

Lopez, G. P. et al., "Preparation of Non-Fouling Biomaterial Surfaces by Plasma Deposition of Poly(Ethylene Glycol) Oligomers and Precursors," Nov., 1989.

Lopez, G. P. et al., "Effect of Reduced Substrate Temperature on Film Chemistry in Plasma Deposition of Organics," Sep., 1989.

Lopez, G. P. et al., "Method of Preparation of Non-Fouling Biomaterial Surfaces by Plasma Deposition of Poly(ethylene Glycol) Oligomers and Precursors," Extended Abstract, American Institute of Chemical Engineers, Nov., 1989.

Ratner, B. D. et al., "Surface Characterization of Hydrogels Prepared by Three Methods," Extended Abstract, American Institute of Chemical Engineers, Dec., 1988.

- POLY(METHYL METHACRYLATE)
- POLYCARBONATE
- HYDROGEL
- SILICONE ELASTOMER
- POLYPROPYLENE
- POLY(METHYL METHACRYLATE)
- POLY(VINYLIDENE FLUORIDE)
- POLYMIDE
- NYLON

SURFACE-MODIFIED SELF-PASSIVATING INTRAOCULAR LENSES

This application is a continuation-in-part of U.S. Ser. No. 07/402,181, filed Aug. 31, 1989, which was allowed on Sep. 10, 1990, now Pat. No. 5,002,794.

Field of the Invention

This invention relates generally to the field of intraocular lenses, and more particularly to intraocular lenses having enhanced biocompatibility after implantation.

Background of the Invention

The Intraocular Lens

Opacification of the eye's crystalline lens, a cataract, is the second leading cause of blindness in the U.S. (1, 2). Worldwide, it has been estimated that 12-15 million people are blind from cataracts making cataract the most prevalent ophthalmic disease (3). It is estimated that at 70 years of age, 90% of the total population suffers considerable loss of vision due to lens changes (4). Due to the high incidence of cataract in the elderly, visual impairment because of cataract is expected to increase significantly during the next five decades as the median age of the population increases.

Cataract is not an affliction restricted to the elderly. Lens opacification is also associated with certain medical conditions such as diabetes, hypocalcemia and uremia. Cataract can additionally be initiated by drugs used in the treatment of glaucoma, hypercholesterolemia and certain steroid hormones (3).

Treatment of cataract has been practiced for centuries using a variety of techniques including medical therapy, couching (suction aspiration of the cataract), intracapsular surgery and extracapsular techniques (4). Removal of the opaque crystalline lens eliminates the problem of cataract; however, since significant dioptric power resides in the lens, its removal results in significant visual disability.

Spectacle correction of aphakia (absence of the crystalline lens) results in visual distortions with various problems due to spherical aberrations, magnification effects, and prismatic distortions. The thick lenses required for visual rehabilitation result in a 33% magnification of retinal image size therefore altering depth perception (5).

Contact lenses yield an improved visual result with approximately a 10% magnification. Since the contact lens moves with the eye, prismatic effects are reduced. However, contact lens use is often difficult for patients, particularly the elderly, due to difficulty with insertion and removal, dry eyes, a low blink rate or poor eyelid function (6).

The concept of an intraocular lens implant for visual rehabilitation is advantageous for several reasons. Lens implantation results in a permanent method of restoring visual acuity. The major theoretical advantage of the intraocular lens (IOL hereinafter) implant is that the principal planes of the implant are very close (rarely coincident) with the principal planes of the removed natural lens. As a result, magnification effects are significantly diminished ($\sim$3-5% magnification).

The concept of an artificial replacement for the cataractous lens was first recorded in the 18th century memoirs of Casanova (7). In 1795, an ophthalmologist named Casaamata unsuccessfully attempted implantation of a glass lens into an eye following cataract removal (8). Aside from the introduction of contact lenses, aphakic correction changed little until the late 1970's. In 1949, the posterior chamber intraocular lens was introduced and first implanted by Dr. Harold Ridley, a British ophthalmologist. Ridley proposed the fabrication of an IOL for posterior chamber placement from Perspex [poly (methyl methacrylate)] following the observation that PMMA fragments embedded in the eyes of WWII fighter pilots resulted in an insignificant tissue reaction (9). The Ridley lens was designed to be similar in shape to the human crystalline lens (4 mm thickness, 9 mm diameter). The Ridley lens however was relatively heavy (112 mg) which often resulted in lens decentration or dislocation.

Since the introduction of the Ridley lens in 1949, a plethora of lens designs have been developed in an attempt to improve lens fixation, simplify implantation and to obtain optimal postoperative outcome. The three basic types of intraocular lenses are classified by site of fixation: 1) anterior chamber, 2) iris supported, and 3) posterior chamber.

Apple (3) divided the evolution of intraocular lenses into 5 generations:

Generation I (1949-1954): Original Ridley Posterior Chamber Lenses

Generation II (1952-1962): Early Anterior Chamber Lenses

Generation III (1953-1973): Iris Supported Lenses

Generation IV (1963-present): Modern Anterior Chamber Lenses

Generation V (1975-present): Modern Posterior Chamber Lenses

Due to the frequency of dislocation of the Ridley lens (Generation 1), implantation of the lens in the anterior chamber was introduced in 1952 (Generation II). A high incidence of corneal endothelial damage resulted from use of this lens due to the steep anterior curvature (10). In an attempt to overcome these complications, iris-supported or iris-fixated IOLs (Generation III) were introduced in 1958 by Binkhorst in an effort to provide firm fixation to the iris and assure good optic centration (11, 12). Numerous postoperative complications such as late endothelial cell loss, dislocation and iris erosion resulted in almost complete discontinuation of this lens type.

Redesigned anterior chamber lenses were introduced in the early 1960's (Generation IV). Correct vaulting and proper sizing resulted in improved longterm results. Approximately 17% of all IOL implantations today are anterior chamber lenses.

The return to Ridley's original idea of posterior chamber lens implantation began in 1975 (13, 14). As a result of the development of lightweight lenses that provide better fixation and the introduction of improved surgical instrumentation and techniques, posterior chamber lens implantation was successfully reintroduced. The posterior chamber IOL allows for lens positioning away from the delicate anterior segment structures including the cornea, aqueous outflow channels, iris, and ciliary body. Implantation of the modern posterior chamber lenses now accounts for greater than 80% of all lenses implanted in the U.S. (1).

In excess of 1 million intraocular lenses are implanted yearly in the U.S. (15). The preferred material used for the optic of the IOL continues to be poly(methyl methacrylate) (PMMA hereinafter) due to its dimensional stability, strength, transparency and relative inertness. PMMA transmits more than 90% of incident light, is lightweight and can be easily machined or molded. Several types of optic configurations are currently used: planoconvex, convex-concave and biconvex. Reports suggesting that near UV light (300-400 nm) could be harmful to ocular tissues (16, 17) prompted the introduction of a UV-absorbing IOL in 1982. UV radiation absorbing molecules or chromatophores have been incorporated in the lens optic polymer to prevent retinal damage caused by solar exposure.

Materials used for lens support structure fabrication (referred to as haptics) have included polypropylene (PP), PMMA, nylon, titanium, platinum, steel and polyimide. Currently, PP and PMMA are the materials of choice. PP has substantial tensile strength and a modulus high enough to support the lens optic at a diameter of 0.15 mm (18), yet is flexible to allow insertion.

New areas of research in IOL development include the development of a soft material lens that can be inserted through a smaller limbal incision in an attempt to reduce the incidence of postoperative astigmatism and shorten procedure time. Silicone and hydrogel [poly (hydroxyethyl methacrylate)] materials are being investigated for this purpose (19, 20). Bifocal and multifocal lenses or lenses that provide refractive correction are also currently being investigated (15).

IOL-Related Inflammation

Postoperative inflammation following the placement of a prosthetic IOL is greater than inflammation following simple cataract extraction (21). Acute inflammation may be manifested in the form of sterile hypopyon, recurrent irititis or in the deposition of pigment and white blood cell clumps on anterior and posterior lens surfaces (22). Chronic inflammation may also occur and can be associated with cystoid macular edema, corneal edema and vitritis (23). The UGH (uveitis, glaucoma, hyphaema) syndrome and CRIS (corneal, retinal inflammatory) syndromes are the most commonly reported IOL-related inflammatory conditions (23). A broad spectrum of responses to IOL implantation are observed, ranging from a thin, optically clear IOL precipitate to a severe inflammatory response resulting in recurrent anterior uveitis. Inflammation and its sequelae are the most common reason for IOL explantation or enucleation (3).

There are a variety of causes of inflammation following IOL implantation (3). Causes of IOL inflammation that are not directly related to the IOL include infectious agents, surgical trauma, or allergic response to crystalline lens cortical remnants. IOL-related causes of inflammation include mechanical irritation caused by IOL tissue contact and chafing, defects in lens design or manufacturing, toxic effects from sterilizing agents or residual polishing compounds, or biocompatibility of lens components.

Inflammation affecting the anterior segment of the eye is indicative of the transient or permanent breakdown of the blood-aqueous barrier (24, 25). Upon breakdown of the blood-aqueous barrier, there is a slowing of cell flow within capillaries and a concurrent increase in capillary wall permeability. Plasma proteins, cells and fluids enter the aqueous directly or via the epithelial lining of the iris and ciliary body. The influx of vascular components into the relatively protein-free, acellular aqueous humor results in the release of inflammatory mediators into the aqueous humor.

The prominent result of the inflammatory process is the occurrence of tissue destruction. Tissue destruction occurs as the result of proteolytic enzyme degradation of collagen and elastin (26). Prostaglandins and leukotrienes also act as inflammatory mediators and chemotactic agents are generally extremely toxic to the retina and corneal endothelium. An additional factor in host tissue destruction is the activation of the complement proteins either by the classical pathway (i.e. antibody/antigen complexes), and/or by the alternate pathway. The complement system of plasma proteins, when activated, can cause a variety of cellular responses including histamine release and/or induction of inflammation.

The sequence of events resulting in IOL-induced inflammation have been postulated by Galin (27). Surgical trauma permits the entry of plasma proteins into the anterior chamber. The IOL then directly or indirectly sustains the activation of complement proteins. C3 fragments affix to the implant surface and C5 fragments are released into the fluid phase. The generation of C5-derived peptides (C5a) increases vascular permeability and results in the leakage of more complement and IgG into the eye leading to clinical signs of uveitis. C5 peptides promote the influx of leukocytes into the chamber. Activated leukocytes react with complement components and IgG to induce tissue injury by releasing lysosomal enzymes. Products of activated leukocytes provoke direct tissue injury and additionally propagate and amplify the inflammatory response.

Surface Passivation By Albumin Adsorption

The initial event that occurs upon exposure of a foreign material (biomaterial) to the physiologic environment is the adsorption of plasma proteins to the material from the fluid phase surrounding the material (28, 29). The high concentration and diffusivity of the plasma proteins compared with the much larger blood cells results in arrival of the plasma proteins at the material surface prior to arrival of the cellular components. The interaction of cellular components with the material surface is therefore mediated through the layer of adsorbed proteins (30). Cellular interactions with interfacial proteins can lead to the activation of the coagulation, complement and fibrinolytic systems (31, 32, 33). Due to the strong influence of the adsorbed protein/material interface on cellular interactions with the material, the composition and organization of the adsorbed protein layer, as influenced by the nature of the material, is of particular interest.

While protein adsorption occurs on all surfaces exposed to biological fluids, differences in the cellular response to various materials are observed. The differential response of tissue to implanted materials is believed to result from differences in the organization of the adsorbed protein layer. Both compositional differences and conformational differences in the adsorbed protein layer are believed to affect cellular interactions (31, 34). The organization of the adsorbed protein layer differs on each type of surface due to differences in the relative affinity of proteins for various surfaces. Substantial differences in the composition of a protein layer adsorbed from plasma to various polymers has been reported (34). The initial composition of the protein layer may also change with time as indicated by time variant adsorption maxima (31, 35). This results in an initial protein layer composed of more abundant surface active proteins, which is later replaced by less abundant proteins with higher surface affinity. The cellular response to a foreign material is believed to be controlled by the presence of specific proteins at sufficiently high surface density and degree of reactivity to elicit a cellular response.

Each plasma cell type possesses cell surface receptors for specific proteins. The sensitivity of cellular interactions to the adsorbed protein layer has been attributed to the enhancement of receptor-protein interaction by the concentration of proteins in the adsorbed layer (30). While not all cells react similarly to a given protein, proteins either enhance or inhibit interactions with cellular components. Fibrinogen enhances platelet adhesion and aggregation and is considered a "reactive" or "adhesive" protein. Fibrinogen is believed to act as a cofactor in inducing platelet aggregation by binding to platelets after they are stimulated by agonists (i.e. adenosine diphosphate) that induce the expression of glycoprotein receptors for fibrinogen on the platelet surface (31). Immunoglobulin G has been demonstrated to promote the adhesion and release of platelets when adsorbed to glass. The cellular reactions to the complement proteins were detailed above. Cold-insoluble globulin protein adsorbed on polyvinyl chloride (PVC) has been shown to enhance thrombus formation (30).

In contrast to the positive cellular response elicited by the proteins listed above, albumin inhibits cellular reactions and is considered a "passivating" or "inert" protein. Surface passivation by an albumin adsorbate has been investigated by several groups. However, none of these studies involved an intraocular lens.

Packham et al. (36) demonstrated that surfaces preadsorbed with albumin showed decreased platelet adhesion compared with surfaces preadsorbed with fibrinogen and IgG.

Van Wachem et al. (37) reported the inhibited adhesion of human endothelial cells by substrates precoated with albumin and IgG, whereas fibronectin coatings promoted cellular adhesion. Albumin has also been shown to decrease red cell adhesion strength to polyethylene (38) and to prevent fibroblast adhesion to tissue culture polystyrene (39).

Lyman (40) evaluated platelet adhesion to hydrophobic polymer surfaces following preadsorption with albumin, IgG and fibrinogen. Platelet adhesion was reduced on surfaces precoated with albumin and was intensified on surfaces precoated with IgG or fibrinogen.

Ihlenfeld (35) investigated the adsorption of albumin, IgG, and fibrinogen to polymeric ex vivo shunt surfaces exposed to flowing blood. Early, predominant fibrinogen adsorption was directly related to thrombogenic and embolic events. Surface passivation with respect to further thrombogenesis was observed for surfaces where initially adsorbed fibrinogen was replaced with albumin and IgG, resulting in a higher fraction of albumin than was present initially.

The use of an albumin coating for surface passivation was unknowingly accomplished in the early 1970's in cardiopulmonary bypass procedures (41). In order to maintain a patient's colloid osmotic pressure at the initiation of bypass, oxygenator circuits were primed with an albumin solution prior to filling with the patient's blood. It was noticed that thrombus formation in the bypass circuit was reduced; however, the effect was inconsistent.

In an effort to improve the thromboresistance of blood detoxification filters, Chang (42) adsorbed albumin directly onto a collodion layer on activated charcoal.

In subsequent studies, the formation of an albumin adsorbate on a polymer surface for surface passivation has been accomplished by several methods. Each of the methods, however, is effective for short-term use only and suffers from additional limitations. Passive exposure of a material to albumin solutions has been attempted (43); however, passively adsorbed albumin layers are weakly bound and are readily desorbed due to fluid shear, protein exchange and/or biological degradation. Spontaneously bound albumin layers adsorbed from solution provide only sparse surface coverage (44) and are not effective in the long-term inhibition of plasma protein adsorption. Methods to immobilize albumin on the material surface prior to implantation, such as protein crosslinking (45) and covalent linkage of albumin to the polymer (46, 47), have been developed. However, crosslinked or covalently bound albumin ultimately denatures.

Enhancement Of Albumin Affinity By Surface Alkylation

While spontaneously adsorbed albumin coatings provided sparse coverage and were easily desorbed, Eberhart (44) noted that such coatings resulted in an inhibition of fibrinogen, gamma globulin and fibronectin adsorption.

In noting that albumin in whole blood has a high affinity for circulating free fatty acids (FFA), Munro proposed covalently binding 16 or 18 carbon alkyl chains to polymer surfaces for the purpose of selectively increasing the affinity of the polymer for albumin (48, 49). The selective adsorption of albumin from blood onto an alkylated polymer had been shown earlier by Plate and Matrosovich (50) in their study of albumin adsorption on alkylated resins for affinity chromatography applications. Munro proposed (51) that a dynamically renewable endogenous albumin adsorbate could be established between the alkylated surface and the blood which would indefinitely mask the substrate from blood-borne host defense activation mechanisms (48, 49, 52). Notably, Munro dealt with reducing thrombogenicity of articles in contact with blood products, and did not disclose any utility in the eye.

The majority of polymers alkylated by the methods described have been polymers used in blood contacting applications for the purpose of improving material thromboresistance. In an attempt to enhance albumin affinity and ultimately improve blood compatibility, alkyl chains of 16 and 18 carbon residues have been covalently attached to polyurethanes (44, 49, 51, 52, 53, 54), polyamides (48), polyesters (48), cellulose acetate (55), Dacron (56) and silicone rubber (57). Alkylation of poly(methyl methacrylate) as described herein has not been previously reported.

Grasel, Pierce and Cooper (58) evaluated the effect of alkyl grafting on the blood compatibility of polyurethane (PU) block copolymers. The deposition of adherent platelets and fibrinogen molecules was measured following blood exposure (1-60 minutes) in a canine ex vivo shunt experiment. A relatively low and constant level of platelet and fibrinogen deposition was noted on the C-18 polyurethane surface compared with the control surface. Platelet attachment and shape-change was surface dependent, with minimal platelet shape change and spreading observed on alkylated surfaces.

While the majority of studies investigating the blood compatibility of alkylated polymers has focused on polyurethanes, alkylated cellulose acetate membranes, Dacron and silicone rubber surfaces have recently been investigated. The albumin adsorption and retention of C-16 alkylated Cuprophane TM dialysis membrane was evaluated (52, 55, 59). In addition, the activation of complement proteins upon exposure to alkylated membranes was evaluated. Albumin adsorption to alkylated Cuprophane TM was not significantly increased over the control surface. Albumin retention following exposure to a moderate fluid shear field and following exposure to a protein denaturant was significantly increased on the alkylated surface indicating stabilization of the adsorbed albumin by interaction with the alkyl chains grafted to the Cuprophane TM surface. Minimal C5 activation was noted on derivatized and control surfaces; however, a significant reduction in C3 activation was observed for the alkylated surface.

The effect of C-16 alkylation of poly(ethylene terephthalate) on albumin adsorption was investigated by Tingey et al. (56). Albumin adsorption from pure solution was reported to be proportional to alkyl chain coverage with a four-fold increase in albumin adsorption observed over underivatized controls.

Albumin adsorption and retention following elution with sodium dodecyl sulfate (SDS) was evaluated on C-16 alkylated silicone rubber films (57). The alkylated silicone rubber was prepared by hydroxylation of a vinyl-methyl silicone co-monomer followed by C-18 acylation of the hydroxylated surface. Both the hydroxylated and alkylated surfaces showed increased albumin adsorption with respect to the control surface. Albumin retention following SDS elution was increased for both the hydroxylated and alkylated surfaces.

Intraocular Lens Surface Modification

The majority of research performed in IOL surface modification has been for the purpose of reducing corneal endothelial cell damage caused by the IOL during implantation. Knight and Link (60) reported a decreased endothelial cell adhesiveness with IOL surfaces onto which hydroxyethyl methacrylate (HEMA) and N-vinyl pyrrolidone (NVP) were radiation grafted. Reich et al. (61) examined the force of adhesion between corneal endothelium and various modified IOL surfaces including plasma deposited NVP, Healon TM, poly HEMA and Duragel TM. Mateo and Ratner (62) investigated the extent of cell adhesion damage to corneal endothelium following contact with PMMA and four types of plasma-deposited polymer coatings on PMMA substrates. Modified surfaces were found to induce a significantly different degree of cell adhesion than that caused by PMMA. Balyeat et al. (63) used a hydrophobic, oleophobic lens coating (IOPTEX Inc.) to reduce corneal endothelial damage compared with an uncoated lens. However, surface analysis studies revealed no surface modification compared to PMMA.

Hofmeister et al., (64) evaluated a hydrophilic graft polymer surface modification (Pharmacia Ophthalmics Inc.) of the PMMA IOL with the intent of producing a surface inhibitive of cell growth. A layer of confluent rabbit epithelial cells was noted on untreated lenses after 8 hours; however, the surface-modified IOL showed no evidence of cell growth.

In an attempt to reduce the degree of adverse reactions (i.e. inflammation) following IOL implantation, Fagerholm et al. (65) investigated a hydrophilic surface-modified IOL that inhibits cell attachment in vivo. The IOL was modified by covalent end-point attachment of heparin to the lens surface. The heparin-modified lenses demonstrated reduced accumulation of inflammatory precipitates when compared with the control IOL surface. In vitro cell adhesion was also reduced for heparin surface-modified lenses.

In U.S. Ser. No. 768,895, Ratner and Mateo disclosed polymeric intraocular lenses modified by a gas plasma deposited fluorocarbon coating. This prior disclosure, however, did not utilize alkyl group containing coatings and did not control the plasma deposition process to reduce monomer fragmentation, as in the present invention.

It can be seen that although progress has been made in IOL fabrication, a need continues to exist for new ways to reduce the clinically observed inflammatory response following implantation of an IOL. In other words, it would be useful to discover new or improved ways to enhance biocompatibility of IOLs.

SUMMARY OF THE INVENTION

The present inventors have discovered that a particular type of surface modification of an intraocular lens can achieve a surface that selectively adsorbs an immunologically non-stimulating protein layer such as albumin upon exposure to the physiological environment, thus rendering the intraocular lens surface less prone to cellular and protein interactions following implantation. The coatings of the present invention comprise a layer of $C_{12}$-$C_{36}$ alkyl chains, which selectively adsorb and retain albumin onto the surface of the IOL. The adsorbed albumin layer diminishes undesirable physiological responses such as inflammation due to implantation of the IOL.

The present invention also involves methods of alkylating the surface of an IOL to produce the above-described coated IOLs. In one preferred method, a plasma deposition process that minimizes fragmentation of the alkyl chains of the coating material is employed to coat a layer of alkyl chains on an IOL. Such a method is disclosed in U.S. Ser. No. 07/402,181, filed Aug. 31, 1989, which was allowed on Sep. 10, 1990. This prior application is hereby incorporated herein by reference. Other methods useful for coating alkyl groups on an IOL include spin coating a polymerized alkyl group containing monomer and reacting a reactive alkyl group containing monomer directly with the surface of an IOL to result in covalent attachment.

BRIEF DESCRIPTION OF THE DRAWINGS

The invention will become better understood by reference to the following drawings, wherein.

DETAILED DESCRIPTION OF THE PREFERRED EMBODIMENTS

The present invention provides novel intraocular lenses, which are alkylated on the surface thereof and new techniques for modifying intraocular lens surfaces with alkyl groups to obtain a surface with increased physiologic biocompatibility.

Intraocular Lenses (IOLs)

As used herein, an "intraocular lens" or "IOL" is a substitute for a normal lens of the eye, which is intended to be implanted in the eye after lens removal. The IOL of this invention may be designed for anterior or posterior chamber implantation, the latter being preferred.

Generally, the IOL comprises a polymeric lens replacement, referred to as an optic. In a preferred embodiment, the IOL is made up of two basic parts: the optic and one or more haptics. A haptic is a support member for the optic that is preferably also polymeric. Currently, in most intraocular lens designs, the optic is supported and held in place by a plurality of haptics. Each of the haptics is attached or secured to the peripheral lens body edge and each is flexible, i.e., yields under pressure, but also will return to its normal extended position once contact pressure has been released. Thus, the haptics have a spring-like quality and are normally composed of a biologically inert plastic material. For purposes of the present invention, when they are present, the haptics may be attached to the lens body by any desirable or convenient means, such as a hole provided in the periphery of the optic, an adhesive, and the like.

Figure 1:
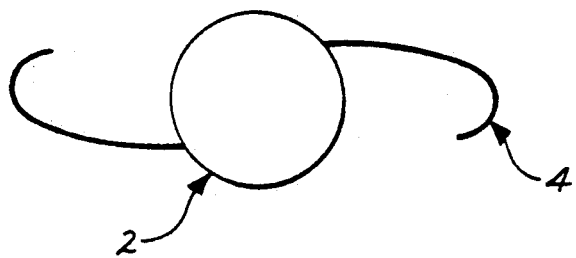
FIG. 1 is a schematic depiction of an intraocular lens (IOL) showing the optic and haptics.

FIG. 1 depicts a preferred IOL, which includes an optic 2 and haptics 4.

The optics of the present invention may be made of any material that is standard in the art of IOLs, or others developed in the future for this purpose. Exemplary materials, which are not intended to be limiting, are: poly(methyl methacrylate) (referred to herein as PMMA), polysulfone, polycarbonate, poly(butyl methacrylate), polyurethane, siloxanes, and the like. The presently preferred optic material is PMMA.

The materials useful for making the IOL may also include additives, such as ultraviolet light absorbers, or they may be otherwise modified to improve their properties as lens replacements. The specific aspects of any such additives or modifications are not critical for the present invention as long as they are compatible with an alkyl coating (described below) and with the intended use as an IOL.

When haptics are present, they may be made of any material standard in the art or others developed in the future that are suitable for this purpose. Typical haptic materials include, but are not limited to, polypropylene, poly(methyl methacrylate), polycarbonate, polyacrylate, poly 2-hydroxyethyl methacrylate, nylon, extruded Teflon TM, stainles steel, platinum, titanium, tantalum, and the like. The composition, number, and shape of the haptics are not critical for purposes of the present invention and may be chosen as desired or necessary as long as they are compatible with the intended use. The preferred haptic material is polypropylene.

For purposes of the present invention, it is also possible to employ intraocular lenses that do not have haptics, and which are supported in the eye by any suitable method or means. When a haptic is present, either or both of the optic and the haptic (or haptics) may be coated by alkyl groups as described herein.

The IOLs of the present invention may be those intended for human or veterinary uses.

Alkyl Coating and Methods of Application

The IOL coating of the present invention may generally be described as an alkyl coating. For purposes of the present invention, an "alkyl coating" is defined as a layer composed of molecules (monomeric, oligomeric, or polymeric), the layer comprising a plurality of alkyl chains having 12 to 36 carbon atoms, which cover substantially the entire exposed surface of the IOL. The alkyl coating should be directly attached to the surface of the IOL, e.g., covalently, or held securely in place on the surface of the IOL as a result of the method of deposition. Covalent attachment will typically apply to alkyl-group containing monomers, whereas non-covalent attachement will typically apply to alkyl-group containing oligomers (2-10 monomeric units) or polymers (>10 monomeric units).

The coating should preferably be substantially homogeneous on the surface of the IOL, as determined by a standard method of chemical or physicochemical analysis, for example, electron spectroscopy for chemical analysis (ESCA), also known as X-ray photoelectron spectroscopy (XPS). The coating on the IOL should also be such that the $C_{12}$–$C_{36}$ alkyl chains are free to extend away from the IOL surface and interact with proteins, such as albumin.

The $C_{12}$–$C_{36}$ alkyl groups may be straight chain, branched, saturated, or unsaturated hydrocarbon chains. The extent to which any branching of the alkyl side chains will be suitable for the present purposes will be dependent on factors such as the ability of the monomers to be polymerized or otherwise coated onto the IOL surface, the affinity of albumin (or similar proteins) to the coated material, and the like. For some purposes, $C_{12}$ or $C_{13}$ alkyl chains may provide advantageous results in terms of biocompatibility, ease of coating, and cost of application. Longer chains (e.g., $\geq C_{18}$) may provide advantages in terms of albumin affinity.

The alkyl groups will usually be attached to a chemical moiety that facilitates attachment to the IOL surface or polymerization. For example, the following are exemplary alkyl-group-containing monomers useful for the present purposes: $C_{12}$–$C_{36}$ alkyl acrylates, $C_{12}$–$C_{36}$ N-alkyl isocyanates, $C_{12}$–$C_{36}$ alkyl vinyl ethers, and $C_{12}$–$C_{36}$ N-alkyl trialkoxysilanes.

In a preferred embodiment, the $C_{12}$–$C_{36}$ alkyl chains are contributed by $C_{12}$–$C_{36}$ alkyl methacrylates, which are polymerized prior to, during, or after coating onto the IOL, or which are covalently attached to the surface of the IOL in monomeric form.

The alkyl group-containing monomers may be polymerized by any standard method and then coated onto the surface of the IOL, such as by centrifugal casting.

Standard centrifugal or spin casting techniques may be used in this method.

A preferred method for coating the IOL involves plasma deposition and polymerization of alkyl group-containing monomers. When the plasma deposition method is employed to coat the IOL, it is important that the monomeric units, especially the alkyl chains thereof, are not significantly fragmented or decomposed. In other words, the plasma deposition method should allow control of the chemical structure of the deposited alkyl group-containing monomers. Intact alkyl side chains present on the surface of the IOL are important for achieving enhanced biocompatibility of the IOL.

The process for the control of chemistry in plasma depositions is based on several factors, previously disclosed in U.S. Ser. No. 07/402,181. Specifically, these include using a low power plasma discharge and simultaneously (or consecutively) condensing nonfragmented precursor gas by maintaining a temperature differential between the temperature ($T_s$) of the substrate (i.e., an IOL) to be coated and the temperature ($T_r$) of the surrounding reactor apparatus, such that $\Delta T = T_s - T_r < 0$.

The monomers that are plasma deposited to form a coating (also referred to herein as a thin film) are referred to as precursors. The precursors of the present invention that are suitable for plasma deposition may vary and can generally be any $C_{12}$–$C_{36}$ alkyl group-containing molecule that has a sufficient vapor pressure under plasma deposition conditions to be adequately deposited on an IOL and thereby enhance adsorption and retention of albumin by the IOL.

The IOL substrate onto which the alkyl group-containing layer is deposited is not necessarily limited other than that it must be compatible with the precursor to be deposited on it and the environment of the plasma deposition technique. A preferred IOL material is PMMA.

The process is conducted in a plasma deposition reactor, modified if necessary to provide for temperature control of the IOL substrate and/or deposition chamber. Generally, since relatively thin coatings are desired, low energy sources will be employed as power sources. A preferred power source is a radio frequency power source. A low power radio frequency power source will generally have an output of from 3 to 200 Watts, preferably 3 to 50 Watts. In addition to radio frequency as a power source, other standard power sources may also be used. In each case, to be compatible with the defined coating chemistry that is sought, the power source must be sufficiently nonenergetic to reduce fragmentation and rearrangement of precursor molecules during deposition. That is, the plasma characteristics should be such that the power level of the plasma (determined by the power supply, precursor type, reactor type, etc.) causes sufficient levels of nonfragmented precursors to be present in the plasma to result in selective condensation.

By a "thin" film as used herein connection with plasma deposition methods is meant a film composed of precursor molecules generally having a thickness of from 5 to 2000 angstroms, preferably 10 to 200 angstroms.

Control of the chemical structure of the thin film is achieved primarily by reducing fragmentation and rearrangement of the precursor molecules so that the precursor molecules are incorporated relatively intact into the thin film as it forms, as compared to conventional techniques. The examples in U.S. Ser. No. 07/402,181 illustrate ways to measure the amount of fragmentation and rearrangement of precursor molecules that has occurred during deposition. These methods are generally based on measurements of physical properties, particularly by way of spectral analysis of the films. A film in which the precursor molecules have undergone reduced fragmentation and rearrangement will have physical properties and spectra that more closely resemble the precursor molecules than films that have been formed by conventional plasma deposition techniques.

The chemical properties of the thin films produced by the present techniques will more closely resemble those of the precursor molecules, due to retention of precursor functional groups, than will thin films produced by conventional plasma deposition techniques.

A semiquantitative method for determining the amount of precursor fragmentation occuring during film deposition involves comparing the XPS spectra of the films with the XPS spectrum of the precursor. Because XPS gives quantitative information on the film's functional groups, the ratio of areas under the XPS spectral peak(s) corresponding to characteristic groups of the film to the total area under several or all XPS peaks, as compared to the analogous ratio for the precursor, can give an indication of the degree of precursor fragmentation. If a specific carbon-containing functionality in the precursor is of interest (e.g., $CH_3$, etc.) the ratio of the quantity of the functionality (area under the appropriate spectral peak) to the total quantity of carbon functionalities in the precursor or film (total area under the XPS spectra peaks) is used. Thus, this ratio will be determined for a film of interest, and the corresponding ratio will be determined for the precursor. A fragmentation factor can then be defined by dividing the ratio corresponding to the precursor into that corresponding to the film. If there is no fragmentation, the two ratios should be equal and, therefore, the fragmentation factor will be equal to 1. If there were total fragmentation, the band corresponding to the functional group of interest would be missing altogether in the film (or be very small). In this case, the fragmentation factor would approach 0. The fragmentation factor will thus range theoretically from 0 to 1, 1 being indicative of a lack of fragmentation and 0 indicating complete fragmentation.

For polymerizable precursors such as an alkyl methacrylates, the present invention will generally produce a film having a fragmentation factor of from 0.8 to 1, preferably 0.9 to 1. Conventional films formed by plasma deposition will have fragmentation factors that are lower than those of the present invention.

The above approach to measuring the degree of fragmentation resulting from a plasma deposition process is only one approach, and other quantitative, semiquantitative, and qualitative approaches to determining degree of fragmentation of the precursor may be utilized, if necessary, to determine the degree of fragmentation. For example, elemental analysis of the precursor and films could be employed as an indicator of degree of fragmentation.

In order to maintain a portion of the apparatus at a higher or lower temperature than ambient temperature, various means of temperature control may be used. Generally, any convenient method of temperature control which is compatible with a plasma deposition process and apparatus may be utilized. Low temperatures may be created by use of liquid nitrogen, a dry ice/acetone bath/an ice/water bath, etc. Higher temperatures may be generated by using any standard heating element, circulating heated liquid, etc. Some variation in temperature during the course of the deposition process or, in a sequential process, during or between deposition steps, is tolerable. Preferably, substantially constant coolant temperatures will be maintained during deposition or between deposition steps. By substantially constant is meant that the temperature does not vary more than ±5° C., preferably ±3° C., most preferably ±1° C. The plasma is a source of energy, hence the substrate temperature which has been equilibrated (to some low value, for instance) before deposition, rises somewhat when the plasma is turned on. Therefore, temperature is generally not constant during deposition. By "ambient" temperature as used herein is meant a temperature of about 21°-25° C.

The condensation temperature of the precursor means the condensation temperature under the conditions in the plasma reactor. Such temperature may be estimated for a given precursor taking into consideration the conditions of pressure, etc. in the reactor during plasma deposition. Because of the complex nature of the plasma, it is usually only possible to estimate the condensation temperature using calculations based on ideal, non-plasma conditions. The condensation temperature will not only depend on precursor pressure, but plasma power levels, etc.

Maintenance of a negative temperature difference or differential ($\Delta T$) between the substrate being treated and the surrounding deposition chamber (chamber walls, electrodes, inlet and outlet lines etc.) is important to all embodiments of this plasma deposition process. The temperatures of the substrate and the chamber walls and the difference between them will depend on the nature of the precursor being used (especially its vapor pressure) and the film qualities desired. This temperature differential must be sufficient so that preferential condensation (or, in some instances, gaseous adsorption) occurs on the substrate to be coated under reaction conditions. To achieve this, the substrate should be maintained near (adsorption) or below (condensation) the condensation temperature of the precursor gas at the working pressure of the reactor so that there is a sufficient concentration of nonfragmented precursor molecules in the vicinity of the growing film to insure the incorporation of desired precursor chemical moieties into the film without excessive fragmentation and rearrangement.

It should be noted that because the plasma is a source of thermal energy, large temperature gradients can be generated between the surface of the substrate where film growth is occurring and the substrate cooling stage. In some instances (e.g., the simultaneous condensation/plasma deposition embodiment), an accurate method of determining substrate surface temperature is desirable to predict the onset of condensation.

For high boiling point precursors—those for which the chamber pressure is higher than the saturation vapor pressure—predictable chemical functionality is achieved by subjecting the uncooled substrate to condensible vapors. Examples of these precursors are alkyl esters of methacrylic acid (e.g., $C_1-C_{25}$ alkyl esters, such as lauryl methacrylate, and octadecyl methacrylate). In this embodiment, the temperature differential between the substrate and the surroundings is maintained by heating all parts of the reactor except the substrate. The chamber must be maintained above the condensation temperature of the precursor to insure that: 1) the system pressure is conducive to maintenance of a stable, low power, low temperature glow discharge (approx. 0.01 to 5 mtorr); 2) inlet lines and outlines do not become fouled with unacceptable amounts of condensate; and 3) there is sufficient vapor pressure of the precursor in the reactor to permit the plasma to ignite and to provide uniform condensation on the substrate.

The use of low power discharges is especially necessary in the simultaneous condensation/plasma deposition mode to insure a sufficient population of unfragmented precursor molecules in the plasma so that condensation can occur. If the power of discharge is high enough to fragment all of the precursor molecules entering it, condensation of the precursor cannot occur. Therefore, a discharge with sufficient intact precursor concentration for condensation, and with the capability to covalently bond precursors to the substrate at the film surface, is most desirable. We have utilized a capacitively coupled external electrode system with a radio frequency (RF) power source to insure low power capability. Other configurations with different frequency power sources (e.g., direct current or alternating current, such as acoustic, microwaves, etc.) may perform suitably. The low power requirement depends not only on the total electrical power supplied to the plasma, but also on the pressure and nature of the precursor (e.g., molecular weight, fragmentation and ionization cross sections). The inventors found that the easiest way to ascertain whether the power level of the plasma is sufficiently low for maintenance of precursor structure is to compare depositions with and without temperature differential at low and high powers. The threshold power limit is dictated by an acceptable level of precursor fragmentation resulting in a desired deposited film functional group concentration. The degree of precursor fragmentation is likely related to the ratio of of power supplied to the total number of molecules in the plasma (i.e., the pressure). The low power requirement also ensures reasonable cooling load on the cooling stage and reduced film damage by energetic ion bombardment. The method disclosed in prior U.S. application Ser. No. 07/402,181, filed Aug. 31, 1989, may be utilized for this plasma deposition process to coat the IOL. This method has an advantage over solution coating methods in that no solvents are involved during coating; this renders the coating method simpler and more economical.

Another method that may be utilized for coating the IOL involves solution covalent attachment of alkyl chain-containing monomers to the IOL surface. In this method, standard solution chemistry may be involved. Usually, a chemically reactive alkyl-group containing donor is employed for this embodiment. A "reactive" $C_{12}-C_{36}$ alkyl group containing monomer is a molecule bearing a chemical moiety that is readily able to form chemical bonds with a surface moiety of the IOL. For example, The IOL may be reacted with one or more $C_{12}-C_{36}$ alkyl isocyanates, $C_{12}-C_{36}$ alkyl trialkoxysilanes, $C_{12}-C_{36}$ alkyl acid chlorides, $C_{12}-C_{36}$ 1,2 epoxides, $C_{12}-C_{36}$ substituted anhydrides, and the like. These molecules react with the surface of the IOL and form chemical bonds to the surface thereof. If necessary or desired, the surface of the IOL may be pretreated (e.g., exposed to ozone or a corona discharge) to enhance its reactivity with a reactive alkyl group containing monomer. The desired result is for the alkyl groups to be bound to the surface of the IOL and capable of interacting with albumin through the alkyl portion so as to increase the retention time of albumin on the surface of the IOL. The coating methods described herein are exemplified below in the Examples section.

Mixtures of different polymers or monomers may also be utilized to coat the surface of the IOL. Copolymers of different monomers may also be employed. Copolymers may be useful in enhancing the compatibility between a polymeric alkyl group containing coating and the surface of the IOL. The first monomer of the copolymer should be a $C_{12}$-$C_{36}$ alkyl group containing monomer (e.g., a $C_{12}$-$C_{36}$ alkyl methacrylate), whereas the second (or additional) monomer(s) should be one(s) that enhance(s) compatibility of the copolymer with the IOL. In the case where the IOL comprises PMMA, the second monomer should preferably be methyl methacrylate. If the IOL is made up of a hydrophilic polymer, then the second monomer of the copolymer should be one capable of hydrogen bonding with the IOL, such as 2-hydroxyethyl methacrylate. The amount of the second monomer should be sufficient to enhance compatibility of the alkyl coating to the IOL without substantially affecting the desired ability of the IOL to adsorb and retain albumin. In preferred embodiments, the second monomer could be contained in a mole percent of 1 to 30% relative to the alkyl group-containing monomer.

The coatings should provide a density of alkyl groups sufficient to significantly enhance the retention time of albumin by the coated IOL surface as compared to the uncoated IOL surface. A coating thickness of 15 to 1000 Å is preferred for the present purposes. A particularly preferred thickness range is 20-200 Å. The thickness of the alkyl coating may be determined by standard methods of chemical analysis, such as ESCA/XPS.

The invention now being generally described, the same will be better understood by reference to certain specific examples, which are included herein to assist one of ordinary skill in the art in making and using the present invention, but which are not intended to be limiting thereof.

EXAMPLES

The methods for coating the alkyl groups onto the IOL surface are exemplified in the following experimental examples.

Centrifugal Casting Method

One technique used for alkylating the IOL surface with the lauryl methacrylate polymer is as follows. Intraocular lenses supplied by Alcon Surgical Inc. (Fort Worth, TX) were used as substrates for coating in all experiments. All lenses used consisted of a poly(methyl methacrylate) optic and poly(propylene) haptics, and were of a planoconvex configuration. The majority of lenses used were 6.0 mm in diameter (Alcon part number 523-00); however, 6.5 mm and 7.0 mm diameter lenses were also used.

Prior to surface coating, lenses were ultrasonically cleaned in a 4% solution of Micro surfactant (International Products Corp., Trenton, NJ) for 30 minutes. The lenses were then ultrasonically cleaned three times for 15 minutes in purified, deionized water and allowed to dry in a laminar flow hood for 24 hours.

The lauryl methacrylate polymer was prepared from a 17% solution of poly(lauryl methacrylate) in toluene (Catalog #168, Scientific Polymer Products, Inc., Ontario, NY). The lauryl methacrylate polymer was precipitated by addition of 2-3 volumes of methanol and then vacuum-dried to constant weight. The polymer was purified by dissolution in spectrophotometric grade toluene and reprecipitation in methanol.

The lauryl methacrylate polymer solution was prepared for centrifugal casting by dissolving the polymer in cyclohexane (Catalog #22,704-8, Aldrich Chemical Co., Milwaukee, WI) to a concentration of 4% (w/w). The solutions were filtered through a disposable 0.5 μm Teflon filter (Catalog #SLSR025N5, Millipore, Bedford, MA) prior to use. Clean intraocular lenses were then coated by placing the lens onto the sample holding platform of a photoresist spinner (Model EC 101, Headway Research Inc., Garland, TX). 20 btl of the 4% polymer solution was pipetted onto the exposed surface of the lens (optic only). The platform was then rotated at 4000 rpm for 20 seconds to centrifugally cast a uniform, thin film onto one side of the lens. The lauryl methacrylate (LMS) coated lens was removed and air-dried in a laminar flow hood for 24 hours. Following the drying period, the uncoated side of the lens was coated with the polymer solution in a similar manner and again air-dried in a laminar flow hood for 24 hours. It is notable that cyclohexane can be used in this lens-coating process. There are few (if any) other solvents that will dissolve C-12 and C-18 methacrylate polymers, and not damage the optical properties of the PMMA substrate.

The technique of IOL alkylation by centrifugally casting an alkyl methacrylate polymer solution onto the lens surface as described above was also utilized to alkylate IOL surfaces with C-18 (octadecyl) alkyl methacrylates. Two C-18 polymers were investigated for IOL alkylation: an octadecyl methacrylate polymer and a copolymer of octadecyl methacrylate and methyl methacrylate. Since adhesion of the pure octadecyl methacrylate polymer to the IOL was anticipated as a potential problem, a copolymer of octadecyl methacrylate and methyl methacrylate was prepared for centrifugal casting onto the IOL surface. It was expected that the poly(methyl methacrylate) component of the copolymer would promote adhesion of the polymer coating to the IOL. Instead of forming a copolymer with methyl methacrylate, compatibility between the polymer of the coating and that of the IOL could also be enhanced by pretreating the IOL surface, e.g., by exposing it to ozone, corona discharge, and the like.

The octadecyl methacrylate polymer was synthesized from a solution of n-octadecyl methacrylate monomer (Catalog #2637, Polysciences, Inc., Warrington, PA) in spectrophotometric grade toluene (Aldrich Chemical Co., Milwaukee, WI) using 2'-2-azobisisobutyronitrile as a catalyst (0.1% w/w). The n-octadecyl methacrylate was purified by distillation and the AIBN catalyst was purified by recrystallization prior to use. The polymerization reaction was conducted at 60° C. for 4 hours under an argon purge. The octadecyl methacrylate polymer was subsequently precipitated into methanol and vacuum-dried.

The octadecyl methacrylate-methyl methacrylate copolymer was synthesized from a mixture of n-octadecyl methacrylate monomer (75% w/w) (Catalog #2637, Polysciences, Inc.) and methyl methacrylate monomer (25% w/w) dissolved in spectrophotometric grade toluene using 2'-2-azobisisobutyronitrile (AIBN) as a catalyst (0.1% w/w). The n-octadecyl methacrylate and methyl methacrylate monomers were purified by distillation prior to use. The AIBN catalyst was purified by recrystallization prior to use. The polymerization reaction was conducted at 60° C. for 5 hours under an argon purge. The copolymer was subsequently precipitated in methanol and vacuum-dried.

The octadecyl methacrylate polymer solutions were prepared for centrifugal casting in the manner described above for the lauryl methacrylate polymer solution. Clean intraocular lenses were then coated with the octadecyl methacrylate solution (ODMS) or the octadecyl methacrylate-methyl methacrylate copolymer solution (ODM-MMA) as previously described.

Plasma Deposition

The second method of IOL surface alkylation investigated in this work involves the simultaneous condensation and plasma-deposition of alkyl methacrylates onto the lens surface using the technique described above and also in U.S. Ser. No. 07/402,181 for the deposition of poly(ethylene glycol) oligomers. Alkylation of the intraocular lens surface was accomplished by the deposition of n-octadecyl methacrylate monomer (Catalog #2637, Polysciences Inc.) or lauryl methacrylate monomer (Catalog #M-116, Scientific Polymer Products, Inc.) as a radio-frequency glow discharge (RFGD) polymer onto the intraocular lens. The simultaneous condensation and plasma-deposition process was utilized to prepare two alkylated intraocular lens surfaces: 1) a plasma-deposited octadecyl methacrylate surface (ODMP) and, 2) a plasma-deposited lauryl methacrylate surface (LMP).

Since the passivating properties of the alkylated lens surface are dependent upon the presence of long, intact alkyl chains on the surface, minimization of precursor fragmentation during plasma deposition is very important. Deposition of the alkyl-containing (e.g., alkyl methacrylates) monomers by conventional deposition techniques would be expected to result in unacceptable levels of alkyl chain fragmentation. Therefore, reduced substrate temperature plasma deposition (i.e., simultaneous condensation/plasma deposition) was investigated in this work for deposition of the alkyl methacrylate monomers.

Results

Exemplary ESCA spectra of coated and uncoated PMMA IOLs are shown in FIGS. 2-8, which are briefly described above and in more detail below.

An ESCA spectrometer (Model SSX-100, Surface Science Laboratories, Mountain View, CA) was used to analyze the surface composition of the various IOL coatings and uncoated IOL surface. The SSX-100 instrument uses a monochromatic aluminum Kα X-ray source (1468±1 eV) and a detection system with a 30° solid angle acceptance lens, a hemispherical analyzer and a position sensitive detector. A low-energy electron flood gun set at 5 eV was used to minimize sample charging. Samples were typically analyzed at a photoelectron take-off angle of 55°. The take-off angle is defined as the angle between the surface normal and the axis of the analyzer lens.

Elements present and their surface composition on the alkylated surfaces were determined by performing survey scans. A survey scan is performed by analyzing a 1000 μm diameter spot at an analyzer pass energy of 150 eV (low resolution) over a 0-1000 eV binding energy range. The experimental peak areas are numerically integrated and normalized with a SSI software package to account for the number of scans, number of channels per eV, the Scofield photoionization cross section and the sampling depth. The normalized peak areas are then used to calculate surface elemental compositions. For calculation of the elemental composition, the detector transmission function was assumed to be constant over the kinetic energy range scanned. The escape depth of the photoelectrons was assumed to vary as $KE^{0.7}$ (66).

More specific information regarding the functional groups present on each surface was obtained by analyzing the same 1000 μm diameter spot at high resolution (25 eV pass energy) over a 20 eV binding energy range around the carbon peak. The high resolution spectra were resolved into individual Gaussian peaks using a least-squares fitting program. C1s spectra were resolved into 4 Gaussian peaks (hydrocarbon, β-shifted hydrocargon, ether and ester peaks) as described by Castner and Ratner (66) for butyl methacrylate polymers. All binding energies were referenced by setting the lowest binding energy component of the resolved C1s peak (corresponding to carbon in a hydrocarbon environment, $CH_x$) to 285.0 eV. Methods of ESCA peak assignment and data analysis have been previously described (67,68).

The C1s core level spectra of the six alkylated surfaces and the control surface (FIGS. 2-8) suggest the presence of at least 3 classes of chemical moieties. The predominant peak, referenced to 285.0 eV binding energy, is due to unsubstituted alphatic and aromatic hydrocarbon species (C—H, C—C). The peak located at 286.7 eV binding energy can be assigned to an ether carbon species (C—O—C) or, in the case of the ODI derivatized surface, this peak can be partially assigned to an amine moiety (C—N). Typical C—N binding energies are 285.8 eV. The peak located at 288.9 eV can be assigned to an ester carbon species (O=C—O) for the alkyl methacrylate surfaces. In the case of the ODI surface, the peak located at 289.5 eV can be assigned to a carbamate species. A fourth peak, located at 285.7 eV, is seen in all spectra except the ODI derivatized surface. This peak can be assigned to a β-shifted hydrocarbon species and is thought to result from a 0.7 eV secondary chemical shift produced by the ester carbon (3.9 eV primary chemical shift) on the backbone alpha carbon (66). In their study of butyl methacrylate polymers, Castner and Ratner (66) have reported that resolution of alkyl methacrylate C1s spectra into 4 peaks (i.e., including the β-shifted hydrocarbon species) resulted in more consistent peak widths, better agreement with polymeric structure and an improved fit. As such, all C1s spectra of methacrylate surfaces evaluated in this work were resolved into 4 peaks.

The C1s spectra of all six alkylated surfaces are seen to be similar with a pronounced hydrocarbon peak indicative of the alkyl moiety. In contrast, the C1s spectrum of uncoated PMMA (FIG. 8) shows the more pronounced ester and ether peaks and a diminished hydrocarbon peak as is predicted by the chemical structure of PMMA.

Since fragmentation of the octadecyl and lauryl chains is possible during the plasma deposition process, the ESCA spectra of the plasma-deposited surfaces and the spin cast surfaces can be compared to estimate the degree to which intact octadecyl/lauryl chains are deposited. Thus, the completely nonfragmented alkylated surface (spin-cast octadecyl methacrylate or lauryl methacrylate) can be compared to the corresponding plasma-deposited surface (i.e., ODMP or LMP) to assess fragmentation.

Figure 2:
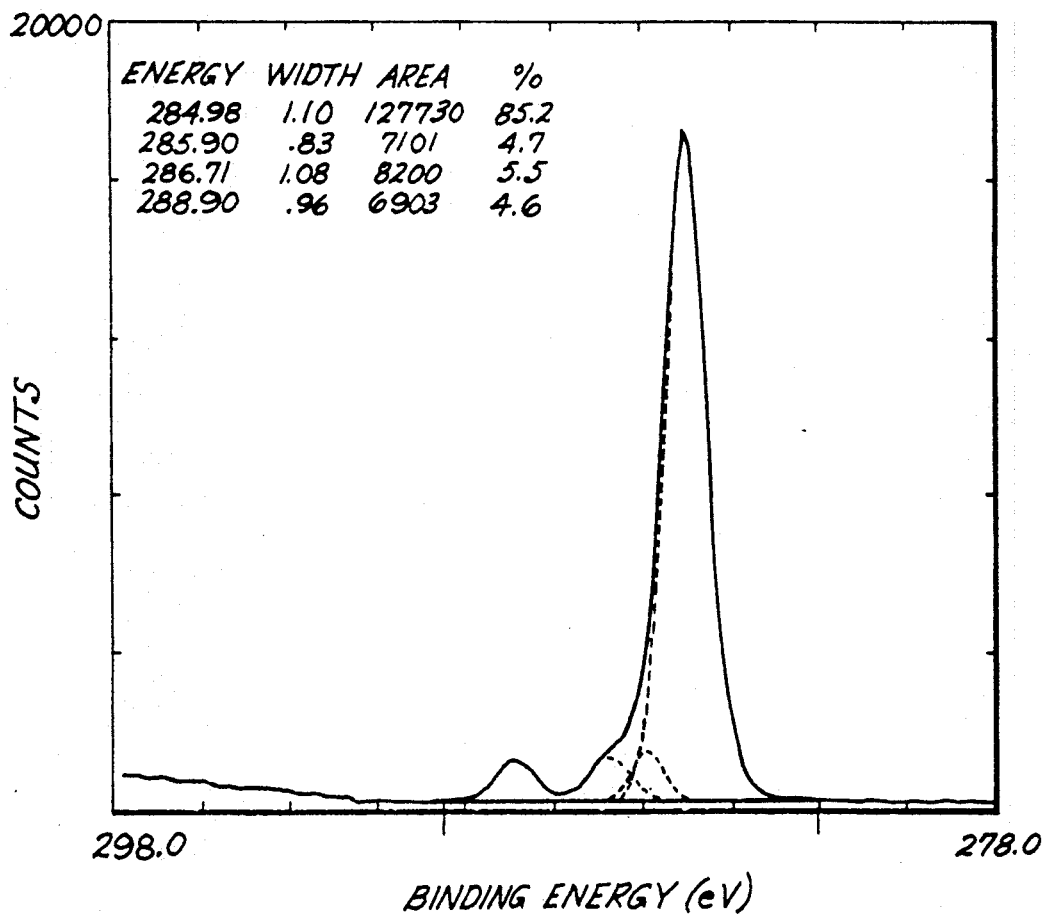
FIG. 2 shows the ESCA C1s spectrum of poly(octadecyl methacrylate) centrifugally cast on an IOL.
Figure 3:
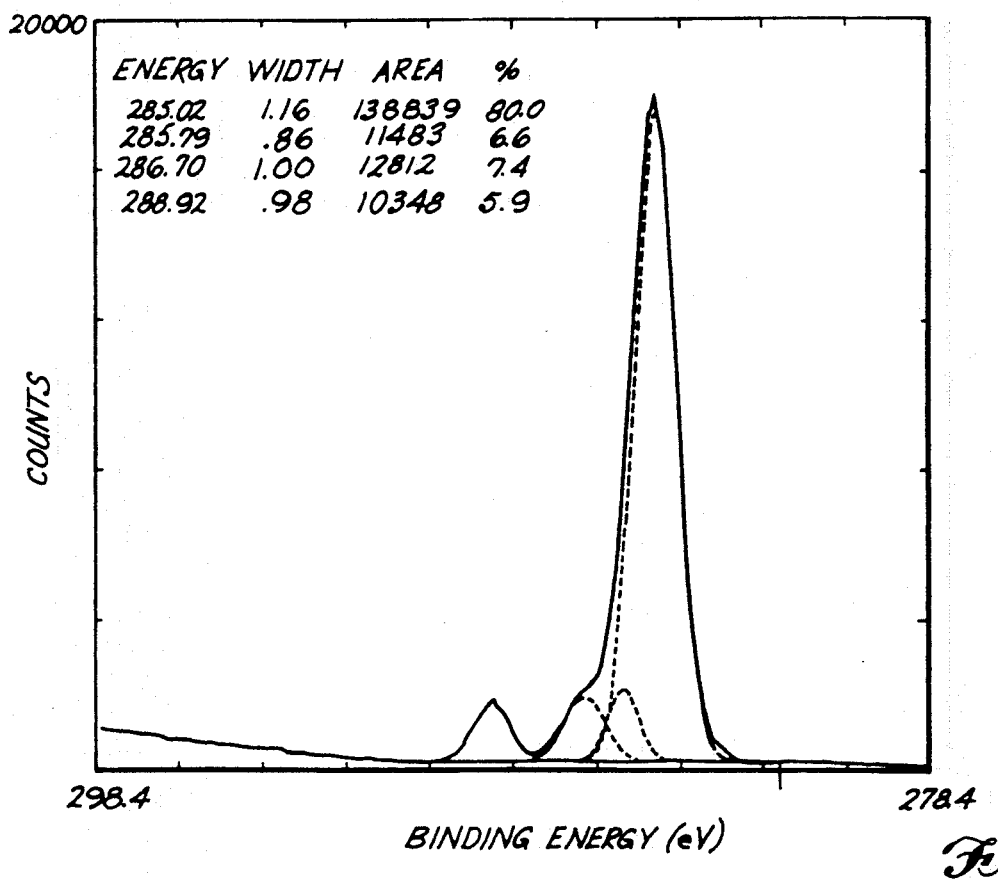
FIG. 3 shows the ESCA C1s spectrum of poly(lauryl methacrylate) centrifugally cast on an IOL.
Figure 4:
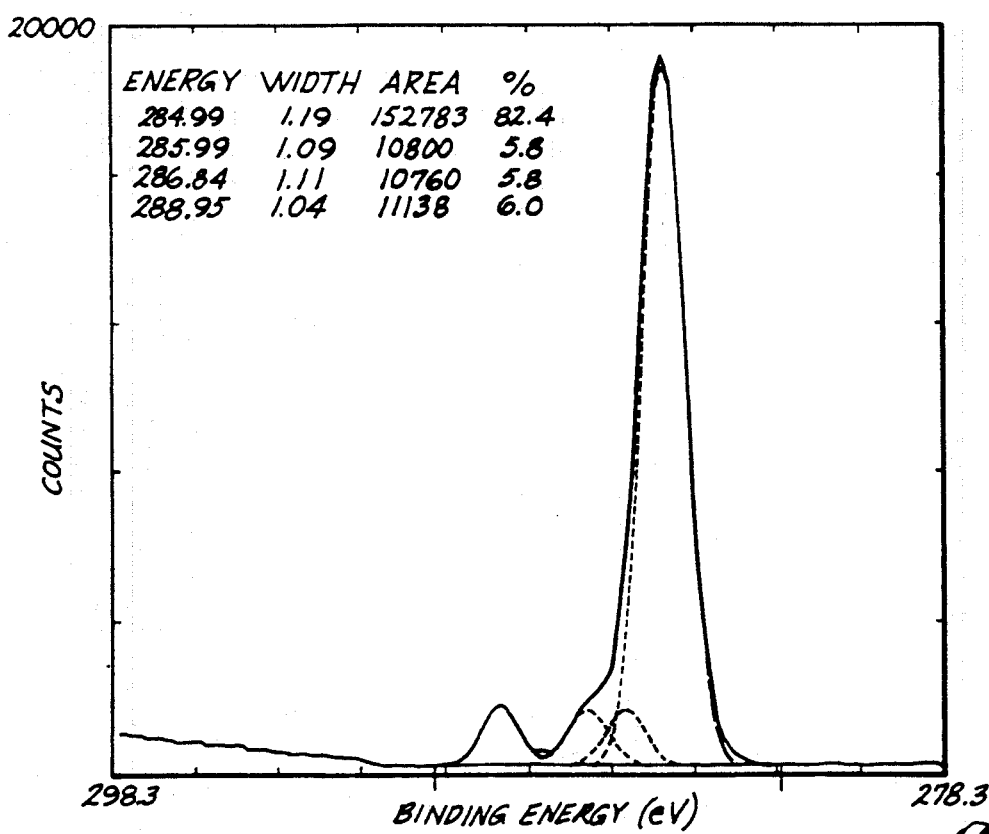
FIG. 4 shows the ESCA C1s spectrum of poly(octadecyl methacrylate-co-methyl methacrylate) centrifugally cast on an IOL.
Figure 5:
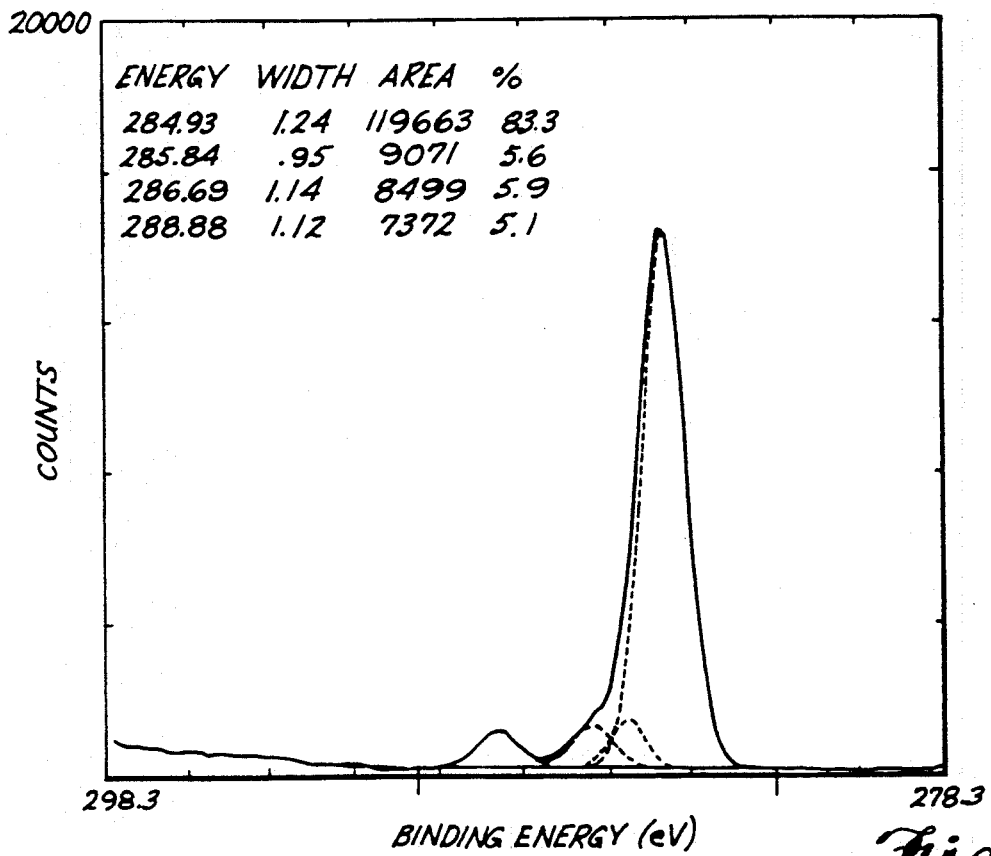
FIG. 5 shows the ESCA C1s spectrum of octadecyl methacrylate plasmadeposited onto an IOL.
Figure 6:
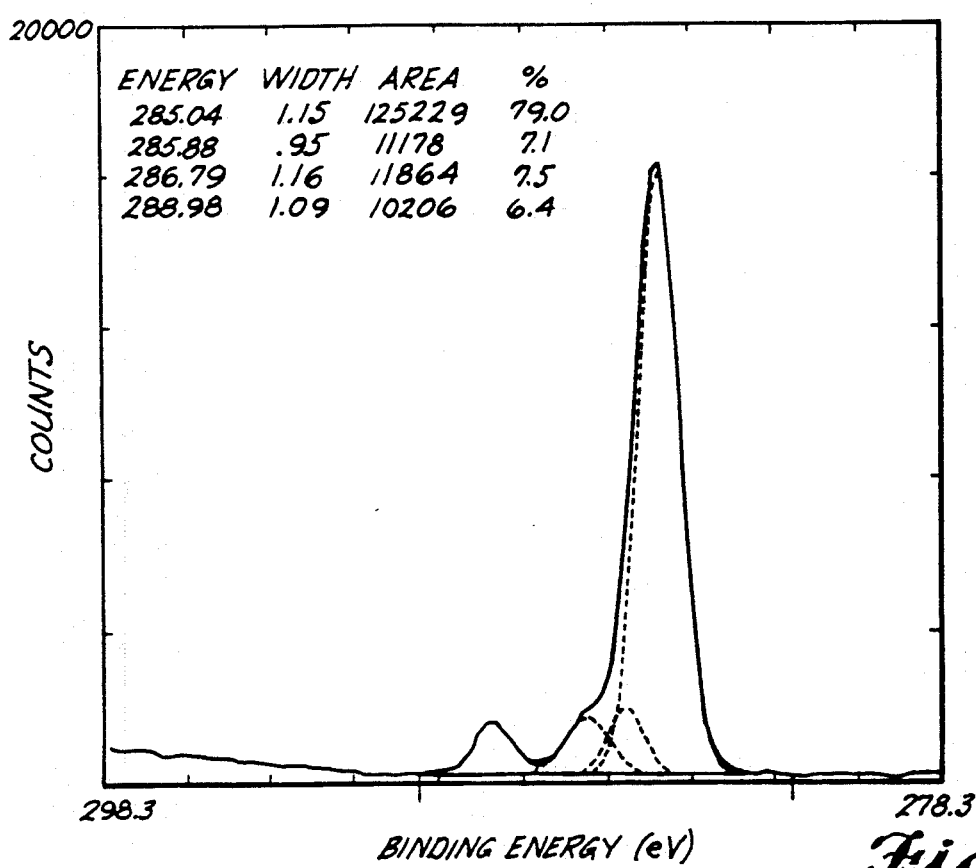
FIG. 6 shows the ESCA C1s spectrum of lauryl methacrylate plasmadeposited onto an IOL.
Figure 7:
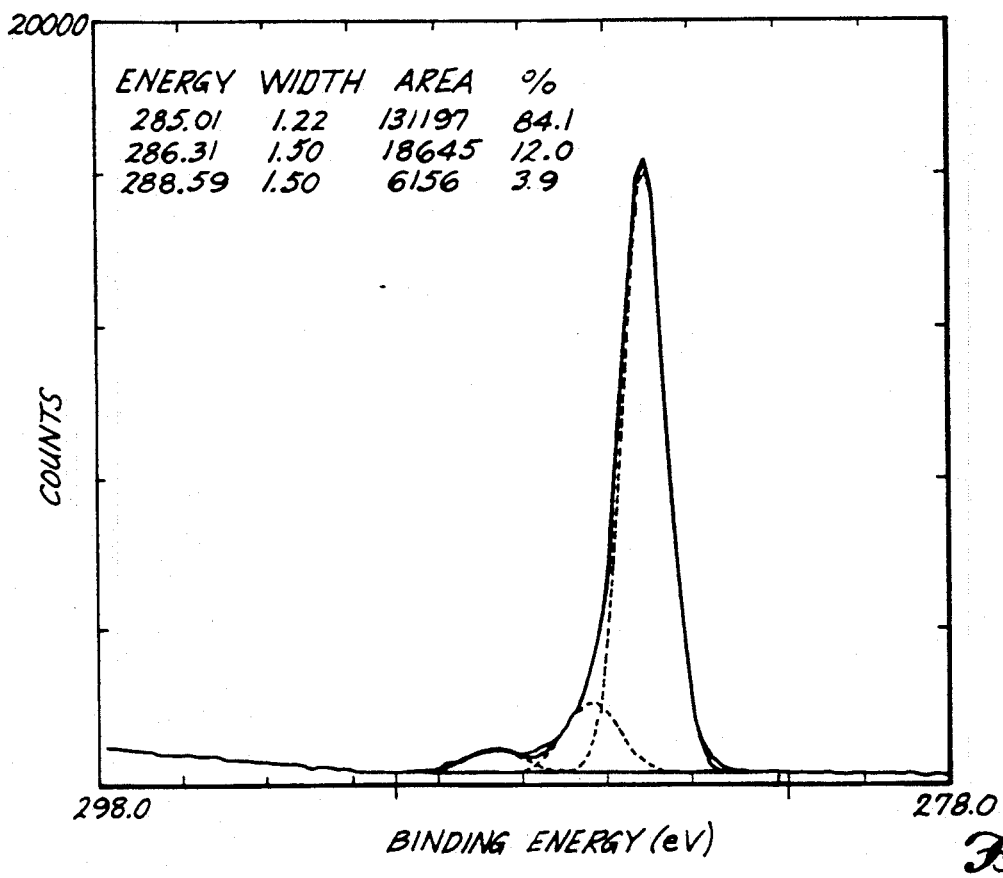
FIG. 7 shows the ESCA C1s spectrum of octadecyl isocyanate solution grafted onto an IOL.
Figure 8:
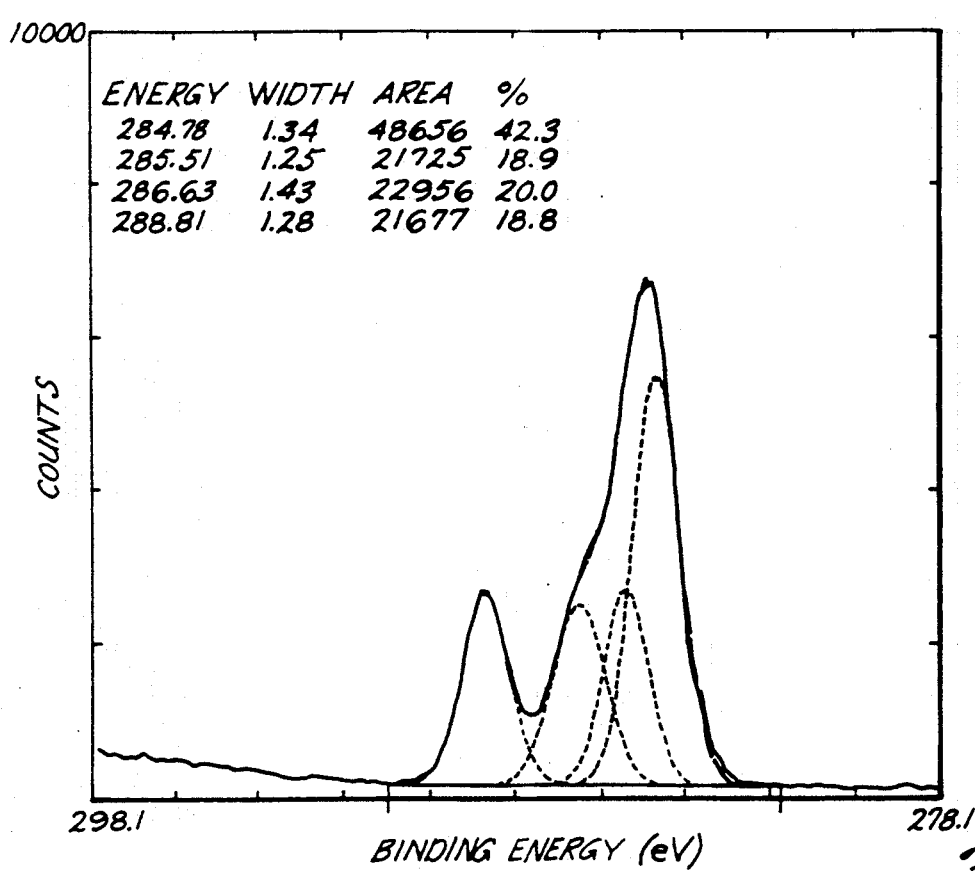
FIG. 8 shows the ESCA C1s spectrum of an uncoated PMMA IOL.

A comparison of FIG. 2 (ODMS spectrum) with FIG. 5 (ODMP spectrum) and FIG. 3 (LMS spectrum) with FIG. 6 (LMP spectrum) indicates that the octadecyl methacrylate and lauryl methacrylate chains are being plasma-deposited with low amounts of fragmentation as evidenced by the similar appearance of the plasma-deposited and spin-cast spectra. While the spectra of many plasma films are reported to be of an ill-defined nature, the spectra of the ODM and LM plasma-deposited films show well-defined peaks with a pronounced hydrocarbon peak. Since the ODM and LM plasma-deposited films show low amounts of fragmentation, it is expected that alkyl functionality levels of the plasma-deposited films will be essentially equivalent to those of the unfragmented models. The low levels of fragmentation observed with these plasma-deposited surfaces are directly attributed to the use of a reduced substrate temperature during the deposition process.

The effect of IOL surface alkylation on albumin adsorption, binding strength and affinity relative to other plasma proteins was assessed in a series of protein interaction studies. These results can be summarized as follows.

Alkylation of the intraocular lens surface resulted in the enhancement of albumin adsorption. This was demonstrated by an increased level of albumin adsorption to the alkylated surfaces (LMS and ODM-MMA) compared with the control surface (PMMA) from complex mixtures such as serum and plasma. Since the adsorption of albumin from a complex mixture involves competition with other plasma proteins, the increased albumin adsorption levels on the alkylated surfaces are indicative of an increased albumin affinity relative to other plasma proteins. An increased albumin affinity resulting from surface alkylation was also demonstrated in competitive protein (binary solution) adsorption studies. Most importantly, alkylated surfaces exhibited surface enrichment of albumin relative to the bulk phase following exposure to plasma, further suggesting an increased albumin affinity resulting from surface alkylation.

Figure 9:
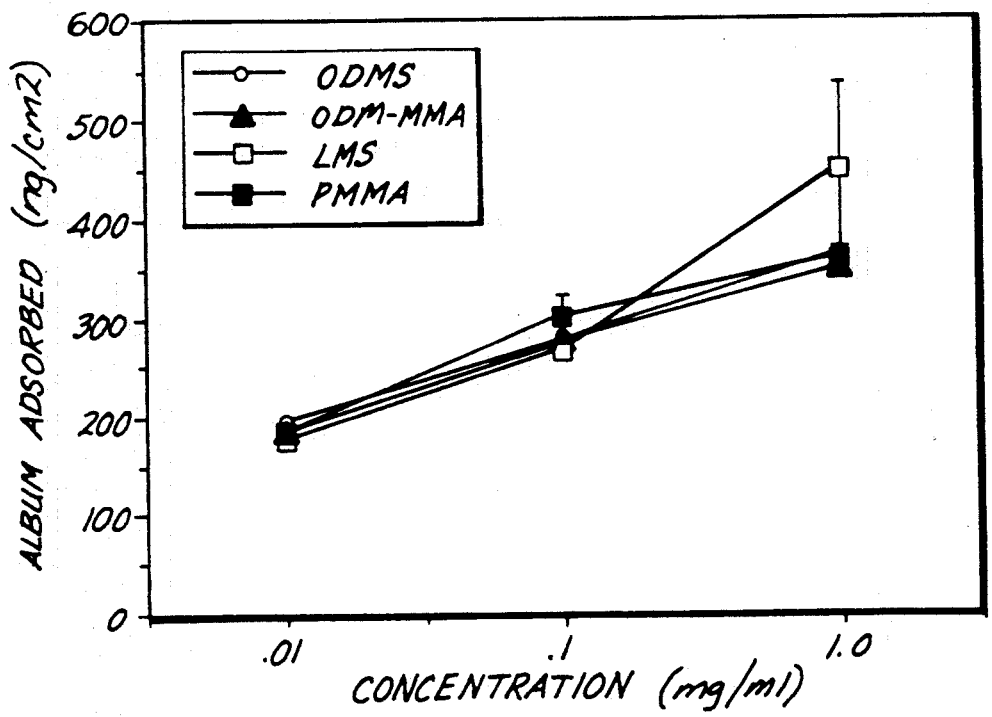
FIG. 9 is a graph showing albumin adsorption to spin-cast surfaces from pure solution.
Figure 10:
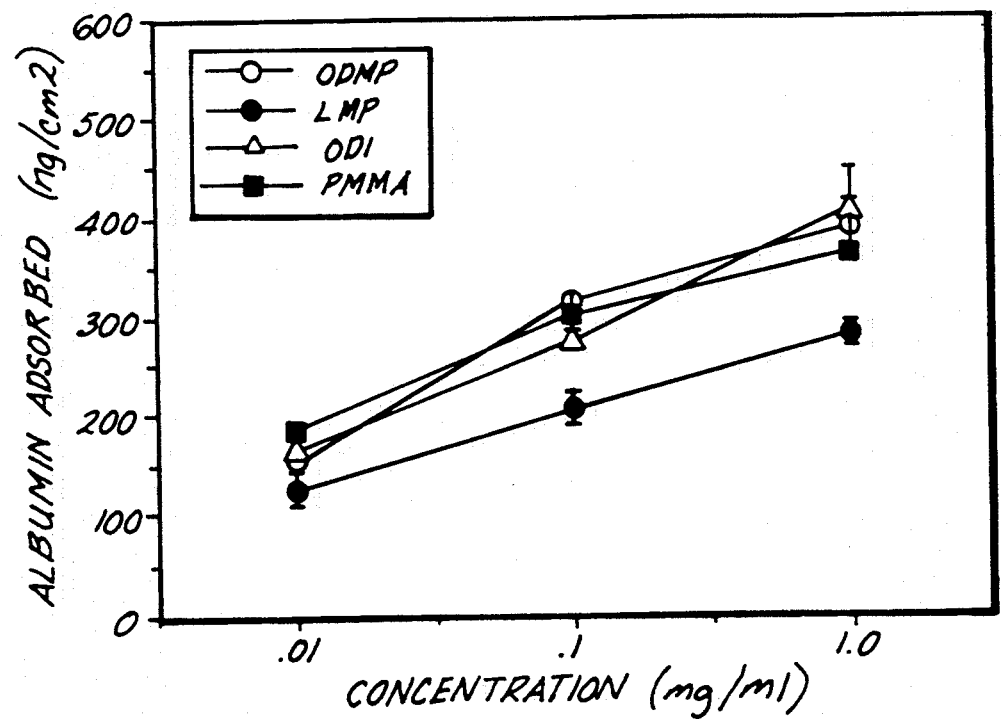
FIG. 10 is a graph demonstrating albumin adsorption to plasma-deposited surfaces from pure solution.

Exemplary experimental data is described as follows:

The albumin adsorption to the spin cast surfaces as a function of the adsorbing solution concentration is presented in FIG. 9 and adsorption to the plasma deposited surfaces is presented in FIG. 10. With the exception of the LMP surface, albumin adsorption is essentially equivalent to all alkylated surfaces and to the control surface. Albumin adsorption on these surfaces ranged from 154–449 $ng/cm^2$ while adsorption to the LMP surface ranged from 126–279 $ng/cm^2$. A linear increase in albumin adsorption with the log of the solution concentration was noted on all surfaces.

Figure 11:
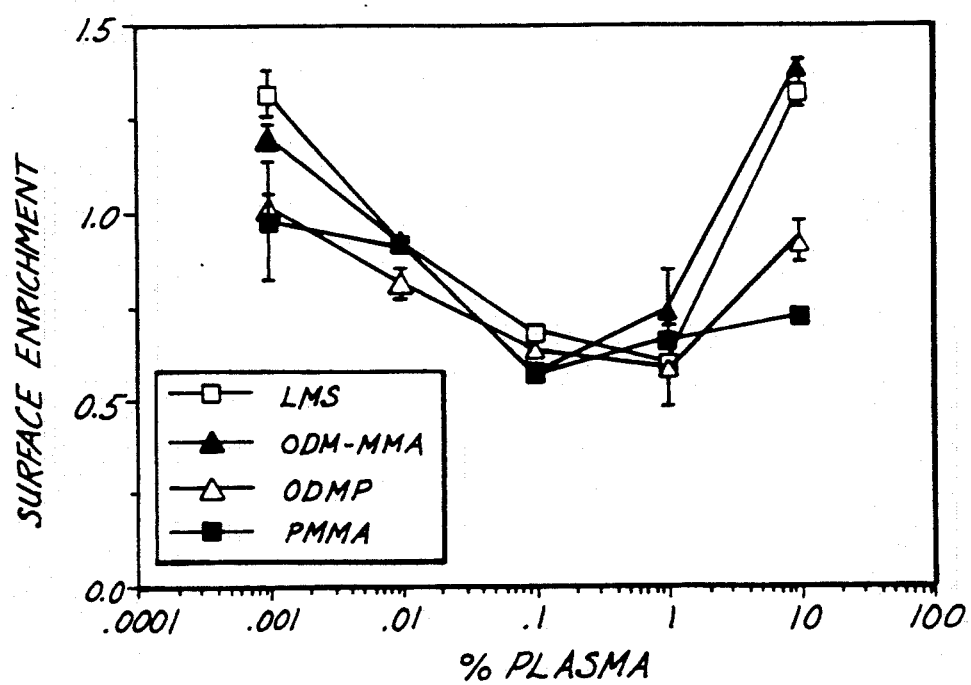
FIG. 11 is a graph showing albumin enrichment on alkylated surfaces following adsorption from plasma.

The surface enrichment values for albumin, fibrinogen and IgG are presented in FIG. 11. As seen in FIG. 11, the ODM-MMA and LMS surfaces result in significant surface albumin enrichment relative to the bulk phase (enrichment >1) at 0.001% and 10% plasma dilutions. Albumin enrichment of these surfaces at 10% plasma was ~0.75. Albumin enrichment values for the alkylated surfaces are greater than enrichment on the PMMA surface for 0.001% ,0.1% and 10% plasma dilutions. At 0.1% and 1% plasma, albumin enrichment values for all surfaces are essentially equivalent.

Figure 12:
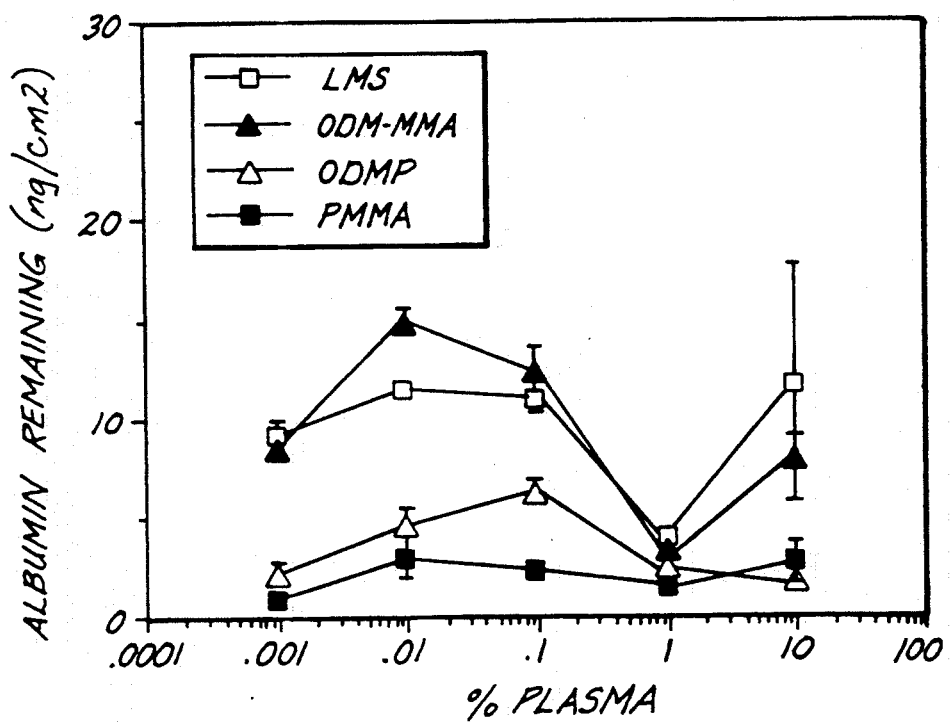
FIG. 12 is a graph showing albumin retention by alkylated surfaces following sodium dodecyl sulfate (SDS) elution.

The amount of protein retained on the IOL surface following elution with SDS was determined and is presented in FIG. 12. As seen in FIG. 12, the amount of albumin retained on the alkylated surfaces was higher than that retained on the PMMA surface. Albumin retention on the PMMA surface was low and ranged from 1–4 $ng/cm^2$. The LMS and ODM-MMA surface resulted in the highest albumin retention of the surfaces tested.

The effect of surface alkylation on the resistance of albumin to solubilization by a surfactant solution (sodium dodecyl sulfate, SDS) was clearly demonstrated in all protein interaction studies. In general, alkylated surfaces demonstrated significant increases in albumin retention following exposure to the surfactant solution compared with the control surface. The increased resistance to SDS solubilization is indicative of an increased binding strength between albumin and the alkylated surface resulting from albumin interaction with the surface grafted alkyl chains at the free fatty acid binding site. Such interaction is also believed to increase the conformational stability of the adsorbed albumin. Increased conformational stability may be an additional factor resulting in the increased resistance to SDS solubilization of albumin adsorbed to alkylated surfaces. A decreased displaceability of albumin by other plasma proteins from the alkylated surfaces was observed at less dilute plasma concentrations and after longer adsorption times. These results give further evidence of an increased binding strength between albumin and the alkylated surface.

IOL surface alkylation with the shorter chain (C-12) alkyl methacrylate polymer resulted in maximal albumin adsorption and/or retention in at least some protein adsorption studies. While C-18 alkylated surfaces were expected to result in maximum albumin affinity, these results suggest that alkylation with shorter alkyl chains may yield improved albumin interaction characteristics. The shorter alkyl chains on the lauryl methacrylate coated surface (and also the C-13 alkyl methacrylate) may be less prone to chain entanglement or chain folding. As a result, the effective length of the alkyl chain available for interaction with albumin may be longer on the lauryl methacrylate surface than on the octadecyl methacrylate surface.

The increased albumin affinity, and binding strength achieved by alkylation of the IOL surface is expected to result in an IOL surface that can selectively adsorb and retain albumin more effectively than the uncoated PMMA IOL. Since cellular interactions with a biomaterial surface are believed to be mediated through the adsorbed protein layer, the enhanced albumin affinity and increased albumin retention achieved through surface alkylation is expected to result in IOL surface passivation following implantation.

In summary, the surface alkylation methods developed in this work differ considerably from existing surface alkylation techniques. In addition, the application of surface alkylation techniques to intraocular lenses has not been previously reported. Finally, the use of a shorter chain (C-12-13) alkyl methacrylate for surface alkylation has not been previously reported. Alkylation with the shorter chain alkyl methacrylate polymers may result in protein interaction characteristics that are improved compared to those achieved with longer chain alkyl methacrylates (C-18 and above) and also compared with other methods of surface alkylation (i.e., octadecyl isocyanate derivatization).

While the invention has been described in conjunction with preferred embodiments, one of ordinary skill after reading the foregoing specification will be able to effect various changes, substitutions of equivalents, and alterations to the subject matter set forth herein. Hence, the invention can be practiced in ways other than those specifically mentioned herein. It is therefore intended that the protection granted by Letters Patent hereon be limited only by the appended claims and equivalents thereof.

CITED PUBLICATIONS

1. Stark W J, Worthen D M, Holladay J T, Bath P E, Jacobs M E, Murray G C, McGhee E T, Talbott, M W, Shipp M D, Thomas N E, Bames R W, Brown D W C, Buxton J N, Reinecke R D, Lao C S, Fischer S. American Academy of Ophthalmology 90: 311–317, 1983.
2. Stark W J. Am J Ophthalmol 98 (2): 238–239, 1985.
3. Apple D J, Mamalis N, Olson R J, Kincaid M C: Intraocular Lenses: Evolution, Designs, Complications, and Pathology. Baltimore: Williams and Wilkins, 1989.
4. Rosen E S, Heining W M, Amott E J (eds): Intraocular Lens Implantation. St. Louis: C V Mosby, 1984.
5. Kraff M C, Sanders D R, Reanan M G. J Cataract Refract Surg 12: 644–650, 1986.
6. Gruber E. Trans Ophthalmol Soc L J K 100: 231–233, 1980.
7. Ascher K W. Am J Ophthalmol 59: 445–446, 1965.
8. Nordlohne M E: The Intraocular Implant Lens: Development and Results with Special Reference to the Binkhorst Lens, ed 2. Baltimore: Williams and Wilkins, 1975.
9. Ridley H. Trans Ophthalmol Soc UK 71: 617–621, 1951.
10. Findley H M, DiIorio R C. J Am Optometric Assoc 55 (11): 811–817, 1984.
11. Binkhorst C D. Trans Ophthalmol Soc UK 79: 569–584, 1959.
12. Binkhorst C D. Am. J Ophthalmol 49: 703–710, 1960.
13. Pearce F L. Br J Ophthalmol 56: 319–331, 1972.
14. Pearce J L. Trans Ophthalmol Soc UK 97: 258–264, 1977.
15. Halter P. Medical Device and Diagnostic Industry 11(3): 28–30, 1989.
16. Pitts D G. J Am Optometric Assoc 52(12): 949–957, 1981.
17. Lanum J. Surv Opthalmol 22: 221–249, 1978.
18. Casella J F. Medical Device and Diagnostic Industry 9(1): 34–38, 1987.
19. Barrett G D, Constable I J, Stewart A D. J Cataract Refract Surg 12: 623–631, 1986.
20. Blumenthal M. In Mazzocco T R, Rajacich G M, Epstein E (eds): Soft Implant Lenses in Cataract Surgery. Thorofare, NJ: Slack, 1986.
21. Galin M A, Obstbaum S A, Boniuk V, et al. Trans Ophthalmol Soc UK 97: 74–77, 1977.
22. Parelman A G. Am Intraocular Implant Soc J 5: 301–306, 1979.
23. Obstbaum S A, Galin M A. Trans Ophthalmol Soc UK 99: 187–191, 1979.
24. Liesegang T J, Bourne W M, Ilstrup D M. Am J Ophthalmol 100: 510–519, 1985.
25. Sanders D R, Spigelman A, Kraff C, Laguros P, Goldstick B, Peyman G A. Arch Ophthalmol 101: 131–133, 1983.
26. Klebanoff S J, Clark R A: The Neutrophil: Function and Clinical Disorders. Amsterdam: North-Holland, 1978.
27. Galin M A, Goldstein I M, Tuberville A, Perex H D, Kaplan H. Arch Ophthalmol 99: 1434–35, 1981.
28. Baier R E, Dutton R C. J Biomed Mater Res 3: 191, 1969.
29. Bruck S D. J Biomed Mater Res 8: 1, 1977.
30. Horbett T A. In Cooper S L, Peppas N A (eds): Biomaterials: Interfacial Phenomena and Applications, ACS Symposium Series 199: 233–244, Washington DC, American Chemical Society, 1982.
31. Lindon J N, McManama G, Kushner L, Merrill E W, Salzman E W. Blood 68(2): 355–362, 1986.
32. Cooper S L, Young B R, Lelah M D. In Salzman E W (ed): Interaction of the Blood with Natural and Artificial Surfaces. New York: Dekker, p 1, 1981.
33. Brash J L. In Salzman E W (ed): Interaction of the Blood with Natural and Artifical Surfaces. New York, Dekker, P 37, 1981.
34. Bohnert J L, Horbett T A. J Colloid Interface Sci 111 (2): 363–377, 1986.
35. Ihlenfeld J V, Cooper S L. J Biomed Mater Res 13: 577–591, 1979.
36. Packham M, Evans G T, Glynn M, Mustard J. J Lab Clin Med 73: 686, 1969.
37. van Wachem P B, Vreriks C M, Beugeling T, Feijn J, Bantjes A, Detmers J P, van Aken W G. J Biomed Mater Res 21: 701–718, 1987.
38. Mohandas N, Hochmuth R, Spaeth E. J Biomed Mater Res 8: 119, 1974.
39. Grinnell F, Feld M K. Cell 17: 117–129, 1979.
40. Lyman D J, Metcalf L C, Albo Jr. D, Richards K F, Lamb J. Trans Amer Soc Artif Intern Organs 20: 474–479, 1974.
41. Webber C E, Garnett E S. J Thor Cardiovasc Surg 65: 234–241, 1973.
42. Chang T M S. Can J Physiol Pharmacol 4: 10–43, 1969.
43. Lyman D J, Knutson K, McNeil B, Shibatani K. Trans Am Soc Artif Intern Organs 21: 49, 1975.
44. Eberhart R C, Lynch M E, Bilge F H, Wassinger J F, Munro M S, Ellsworth S R, Quattrone A J. In Cooper S L, Peppas N A (eds): Biomaterials: Interfacial Phenomena and Applications, ACS Symposium Series 199: 293–315, Washington DC, American Chemical Society, 1982.
45. Kambic H, Barenburg S, Harasaki H, Gibbons D, Kiraly R, Nose Y. Trans Am Soc Artif Intern Organs 24: 426, 1978.
46. Hoffman A S, Schmer G, Harris C, Kraft W G. Trans Am Soc Artif Intern Organs 18: 10, 1972.
47. Imai Y, Tajima K, Nose Y. Trans Am Soc Arter Intern Organs 17: 6–31, 1971.
48. Munro M S, Quattrone A J, Ellsworth S R, Kulkarni P, Eberhart R C. Trans Am Soc Artif Intern Organs 27: 499–503, 1981.
49. Munro M S, Eberhart R C, Naki N J, Brink B E, Fry W J. ASAIO Journal 6: 65–75, 1983.
50. Plate N A, Matrosovich M N. Doklady Akad Nauk SSSR 229: 496–499, 1976.
51. Eberhart R C, Munro M S, Williams G B, Kulkarni P V, Shannon Jr. W A, Brink B E, Fry W J. Artificial Organs 11 (5): 375–382, 1987.
52. Eberhart R C, Munro M S, Frautschi J R, Lubin M, Clubb F J, Miller C W, Sevastianov V I. Ann NY Acad Sci 516: 78–95, 1987.
53. Riccitelli S D, Schlatterer R G, Hendrix J A, Williams G B, Eberhart E C. Trans ASAIO 31: 250–256, 1985.

54. Pitt W G, Cooper S L. J Biomed Mater Res 22: 359-382, 1988.
55. Frautschi J R, Munro M S, Lloyd D R, Eberhart R C. Trans ASAIO 29: 242-244, 1983.
56. Tingey K G, Frautschi J R, Lloyd D R, Eberhart R C. Trans Am Soc Biomat 9: 125, 1986.
57. Tsai C C, Frautschi J R, Eberhart R C. Trans ASAIO 34: 559, 1988.
58. Grasel T G, Pierce J A, Cooper S L. J Biomed Mater Res 21: 815-842, 1987.
59. Frautschi J R, Eberhart R C. 13th Annual Meeting of Society for Biomaterials NY, 6/87, p 125.
60. Knight P M, Link W J. AM Intra-Ocular Implant Soc J 5: 123, 1979.
61. Reich S, Levy M, Meshorer A, Blumenthal M, Yalon M. J Biomed Mater Res 18: 737, 1984.
62. Mateo N B, Ratner B D. Invest Opthalmol Vis Sci 30 (5): 63-70, 1989.
63. Balyeat H D, Norquist R E, Lemer M P, Gupta A. J Cataract Refract Surg 15: 491-494, 1989.
64. Hofneister F, Goldberg E P, Yahiaoui A, Sheets Jr. J W, Yalon M. 15th Annual Meeting of the Society for Biomaterials 5/89, p 19.
65. Fagerholm P, Bjorklund H, Holmberg A, Larsson R, Lydahl E, Philipson B, Selen G. J Cataract Refract Surg 15: 485-490, 1989.
66. Castner D G, Ratner B D. Surface and Interface Analysis 15: 479-486, 1990.
67. Ratner B D, McElroy B J. In Gendreau R M (ed): Spectroscopy in the Biomedical Sciences. Boca Raton, FL: CRC Press Inc. Chap 5. p 107-140, 1986.
68. Dilks A. In Baker A D, Brundle C R (eds): Electron Spectroscopy: Theory, Techniques, and Applications. New York: Academic Press, Vol. 4 p 277-359, 1981.

The embodiments of the invention in which an exclusive property or privilege is claimed are defined as follows:

1. An intraocular lens, comprising an optic bearing a coating comprising $C_{12}$-$C_{36}$ alkyl groups, whereby said optic exhibits enhanced ability to adsorb and retain albumin.

2. An intraocular lens according to claim 1, which further comprises one or more haptics attached to said optic for use in securing or positioning said optic in an eye of a patient.

3. An intraocular lens according to claim 2, wherein said one or more haptics also bear a coating comprising $C_{12}$-$C_{36}$ alkyl groups to thereby enhance the ability of said one or more haptics to adsorb and retain albumin.

4. An intraocular lens according to claim 1, wherein said optic comprises poly(methyl methacrylate).

5. An intraocular lens according to claim 1, wherein said coating comprises a mixture of monomeric, oligomeric, or polymeric $C_{12}$-$C_{36}$ alkyl methacrylates.

6. An intraocular lens according to claim 5, wherein said alkyl methacrylate is lauryl or octadecyl methacrylate or a mixture thereof.

7. An intraocular lens according to claim 5, wherein said alkyl methacrylate is polymerized.

8. An intraocular lens according to claim 7, wherein said polymerized alkyl methacrylate is a copolymer of a $C_{12}$-$C_{36}$ alkyl methacrylate and methyl methacrylate.

9. An intraocular lens according to claim 1, wherein said intraocular lens comprises an optic made of poly (methyl methacrylate) coated with one or a mixture of monomeric, oligomeric, or polymeric $C_{12}$-$C_{36}$ alkyl methacrylates.

10. An intraocular lens according to claim 9, wherein said one or a mixture of $C_{12}$-$C_{36}$ methacrylates are coated on said optic by centrifugal spin casting.

11. An intraocular lens according to claim 9, wherein said one or a mixture of $C_{12}$-$C_{36}$ alkyl methacrylates are coated on said optic by a plasma deposition technique in a deposition chamber, wherein a temperature differential is created between the optic and said deposition chamber sufficient to cause a $C_{12}$-$C_{36}$ alkyl methacrylate monomer to preferentially condense or adsorb and then polymerize on said optic, thereby resulting in a coating on said optic that enhances adsorption and retention of albumin thereon.

12. A method of enhancing biocompatability of an intraocular lens comprising an optic, which method comprises applying to said optic a coating comprising $C_{12}$-$C_{36}$ alkyl groups, whereby said optic exhibits enhanced ability to adsorb and retain albumin.

13. A method according to claim 12, wherein said coating comprises a $C_{12}$-$C_{36}$ alkyl methacrylate monomer, oligomer, or polymer.

14. A method according to claim 12, wherein said coating is applied by spin casting a polymeric $C_{12}$-$C_{36}$ alkyl methacrylate on said optic.

15. A method according to claim 12, wherein said coating is applied by plasma deposition of $C_{12}$-$C_{36}$ alkyl methacrylate monomers on the surface of said optic, under conditions whereby the alkyl groups are substantially unfragmented.

16. A method according to claim 15, wherein said plasma deposition is carried out in a deposition chamber wherein there is a temperature differential between said optic and said deposition chamber sufficient to cause said monomers to preferentially condense or adsorb and then to polymerize on said optic, thereby resulting in a coating on said optic that enhances adsorption and retention of albumin on said optic.

17. A method according to claim 12, wherein said optic comprises poly (methyl methacrylate).

18. A method according to claim 12, wherein said intraocular lens further comprises one or more haptics attached to said optic for use in securing or positioning said optic in an eye of a patient.

19. A method according to claim 18, wherein said one or more haptics also bear a coating comprising $C_{12}$-$C_{36}$ alkyl groups.

* * * * *

UNITED STATES PATENT AND TRADEMARK OFFICE
CERTIFICATE OF CORRECTION

PATENT NO. : 5,171,267
DATED : December 15, 1992
INVENTOR(S) : B.D. Ratner et al.

It is certified that error appears in the above-identified patent and that said Letters Patent is hereby corrected as shown below:

| COLUMN | LINE | |
|---|---|---|
| 2 | 50 | "longterm" should read --long-term-- |
| 8 | 64 | "plasmadeposited" should read --plasma-deposited-- |
| 8 | 66 | "plasmadeposited" should read --plasma-deposited-- |
| 10 | 1 | "stainles" should read --stainless-- |
| 10 | 29 | "attachement" should read --attachment-- |
| 11 | 58 | after "herein" insert --in-- |
| 12 | 17 | "occuring" should read --occurring-- |
| 18 | 14-15 | "hydro-cargon" should read --hydrocarbon-- |
| 23 | 23 | "Hofneister" should read --Hoftneister-- |

Signed and Sealed this

Twenty-third Day of November, 1993

*Attest:*

BRUCE LEHMAN

*Attesting Officer*   *Commissioner of Patents and Trademarks*